United States Patent
Mitsudera

(10) Patent No.: US 8,344,163 B2
(45) Date of Patent: Jan. 1, 2013

(54) NITRILE COMPOUND AND ITS USE FOR CONTROL OF ARTHROPOD PEST

(75) Inventor: Hiromasa Mitsudera, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 129 days.

(21) Appl. No.: 12/933,338

(22) PCT Filed: Mar. 18, 2009

(86) PCT No.: PCT/JP2009/056028
§ 371 (c)(1),
(2), (4) Date: Oct. 5, 2010

(87) PCT Pub. No.: WO2009/116687
PCT Pub. Date: Sep. 24, 2009

(65) Prior Publication Data
US 2011/0021627 A1  Jan. 27, 2011

(30) Foreign Application Priority Data

Mar. 19, 2008 (JP) ................... 2008-071101
Jan. 27, 2009 (JP) ................... 2009-015105

(51) Int. Cl.
*A01N 29/02* (2006.01)
*C07C 19/10* (2006.01)
*C07D 339/02* (2006.01)

(52) U.S. Cl. ............ 549/39; 549/90; 549/434; 549/546; 558/430; 558/432; 558/433; 558/434; 558/428

(58) Field of Classification Search ........................ None
See application file for complete search history.

(56) References Cited

U.S. PATENT DOCUMENTS
2004/0138065 A1  7/2004 Otaka et al.

FOREIGN PATENT DOCUMENTS
WO  WO 2005/063694 A1  7/2005

OTHER PUBLICATIONS

International Preliminary Report on Patentability (Form PCT/IB/373) and Written Opinion of the International Searching Authority (Form PCT/ISA/237) issued on Sep. 21, 2010 in PCT/JP2009/056028.
International Search Report for PCT/JP2009/056028 mailed Sep. 11, 2009.
Sheverdov et al., "Reaction of α-β-unsaturated ketones with tetracyanoethylene", Tetrahedron, vol. 57, No. 27, 2001, pp. 5815-5824.
Office Action for corresponding Egyptian Patent Application No. PCT2010091574, dated Mar. 27, 2012.

*Primary Examiner* — Kamal Saeed
*Assistant Examiner* — Nyeemah A Grazier
(74) *Attorney, Agent, or Firm* — Birch, Stewart, Kolasch & Birch, LLP

(57) ABSTRACT

There is provided a nitrile compound having an excellent controlling effect on arthropod pests represented by the formula (I): wherein m represents in integer of 0 to 4; n represents an integer of 1 to 4; q represents an integer of 0 to 4; Q represents a C1-C4 fluoroalkyl group; Z represents an optionally substituted C2-C6 alkynyl group or a =N—OR$_3$ group; R$_1$ and R$_2$ independently represent a monovalent C1-C4 chain hydrocarbon group optionally substituted with a halogen atom, etc.; and A represents an optionally substituted monovalent C1-C6 chain hydrocarbon group, etc.

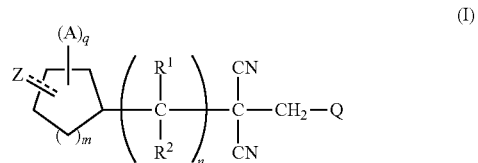

10 Claims, No Drawings

NITRILE COMPOUND AND ITS USE FOR CONTROL OF ARTHROPOD PEST

TECHNICAL FIELD

The present invention relates to a nitrile compound having a fluoroalkyl group and its use for control of arthropod pests.

BACKGROUND ART

Hitherto, there have been provided compounds for control of arthropod pests such as insects and mites, and control methods using the compounds. For example, JP-A 2006-124367 discloses that a certain nitrile compound has an arthropod pest-controlling effect.

DISCLOSURE OF INVENTION

An object of the present invention is to provide a compound having excellent control effect on arthropod pests, and the use of the compound for control of arthropod pests.

The present inventors have intensively studied to find out a compound having an excellent controlling effect on arthropod pests. As a result, they have found that a nitrile compound represented by the following formula (I) has an excellent controlling activity against arthropod pests such as insects and mites, and thus the present invention has been completed.

The present invention provides:
(1) A nitrile compound represented by the formula (I):

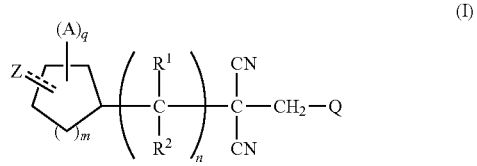

wherein m represents an integer of 0 to 4; n represents an integer of 0.1 to 4; q represents an integer of 0 to 4;
Q represents a C1-C4 fluoroalkyl group;
Z represents a $=N-OR^3$ group, or a C2-C6 alkynyl group optionally substituted with a group selected from the group L;
$R^1$ and $R^2$ independently represent $-C(=G)R^5$, a cyano group, a halogen atom, a hydrogen atom, or a monovalent C1-C4 chain hydrocarbon group optionally substituted with a halogen atom;
A represents $-OR^6$, $-SR^6$, $-S(=O)R^6$, $-S(=O)_2R^6$, $-C(=O)R^7$, $-OC(=O)R^8$, a halogen atom, a cyano group, a hydroxyl group, a monovalent C1-C6 chain hydrocarbon group optionally substituted with a group selected from the group L, or a C3-C6 cycloalkyl group optionally substituted with halogen atom, and when q is 2 or more, two A's optionally form together a C2-C6 alkanediyl group, a C4-C6 alkenediyl group, -G-, $-G-T^1-G-$, or $-G-T^1-G-T^2-$;
said C2-C6 alkanediyl group or said C4-C6 alkenediyl group is optionally substituted with a group selected from the group L; G represents an oxygen atom or a sulfur atom;
$T^1$ and $T^2$ independently represent a methylene group or a C2-C6 alkanediyl group;
$R^3$ represents a hydrogen atom, or a C1-C6 chain hydrocarbon group optionally substituted with a halogen atom;
$R^5$ represents a hydroxyl group, an amino group, a C2-C5 cyclic amino group, a hydrogen atom, a C1-C4 alkyl group optionally substituted with a halogen atom, a C1-C4 alkoxy group optionally substituted with a halogen atom, a C3-C6 alkenyloxy group optionally substituted with a halogen atom, a C3-C6 alkynyloxy group optionally substituted with a halogen atom, a C1-C4 alkylamino group optionally substituted with a halogen atom, or a di(C1-C4 alkyl)amino group optionally substituted with a halogen atom;
$R^6$ represents a C1-C4 alkyl group optionally substituted with a halogen atom, or a C3-C6 cycloalkyl group optionally substituted with a halogen atom;
the group L consists of a hydroxyl group, $-N(R^9)R^{10}$, a C2-C5 cyclic amino group, $-C(=O)R^7$, $-OC(=O)R^6$, a halogen atom, a C1-C4 alkoxy group optionally substituted with a halogen atom, a C3-C6 alkenyloxy group optionally substituted with a halogen atom, and a C3-C6 alkynyloxy group optionally substituted with a halogen atom;
$R^7$ represents a hydroxyl group, a C2-C5 cyclic amino group, an amino group, a hydrogen atom, a C1-C4 alkoxy group optionally substituted with a halogen atom, a C3-C6 alkenyloxy group optionally substituted with a halogen atom, a C3-C6 alkynyloxy group optionally substituted with a halogen atom, a C1-C4 alkylamino group optionally substituted with a halogen atom, a di(C1-C4 alkyl)amino group optionally substituted with a halogen atom, or a C1-C4 alkyl group optionally substituted with a halogen atom;
$R^8$ represents a C2-C5 cyclic amino group, an amino group, a hydrogen atom, a C1-C4 alkoxy group optionally substituted with a halogen atom, a C3-C6 alkenyloxy group optionally substituted with a halogen atom, a C3-C6 alkynyloxy group optionally substituted with a halogen atom, a C1-C4 alkylamino group optionally substituted with a halogen atom, a di(C1-C4 alkyl)amino group optionally substituted with a halogen atom, or a C1-C4 alkyl group optionally substituted with a halogen atom; and
$R^9$ and $R^{10}$ independently represent a hydrogen atom, a C1-C4 alkyl group optionally substituted with a halogen atom, a C3-C6 alkenyl group optionally substituted with a halogen atom, a C3-C6 alkynyl group optionally substituted with a halogen atom, a C3-C6 cycloalkyl group optionally substituted with a halogen atom, or a phenyl group optionally substituted with a halogen atom (hereinafter, referred to as "the compound of the present invention");
(2) The nitrile compound according to the above (1), wherein Z is the C2-C5 alkynyl group optionally substituted with a group selected from the group L;
(3) The nitrile compound according to the above (1), wherein Z is a $-C\equiv C-R^4$ group and $R^4$ is a C1-C4 alkyl group or a hydrogen atom;
(4) The nitrile compound according to the above (1), wherein Z is an ethynyl group;
(5) The nitrile compound according to the above (1), wherein Z is the $=N-OR^3$ group and $R^3$ is the C1-C6 chain hydrocarbon group;
(6) The nitrile compound according to any one of the above (1) to (5), wherein m is 2;
(7) The nitrile compound according to any one of the above (1) to (6), wherein Q is a 2,2,2-trifluoromethyl group;
(8) The nitrile compound according to any one of the above (1) to (7), wherein n is 1;
(9) The nitrile compound according to any one of the above (1) to (8), wherein n is 1 and $R^1$ and $R^2$ are hydrogen atoms;
(10) A pesticidal composition comprising the nitrile compound according to any one of the above (1) to (9) as an active ingredient; and
(11) A method for controlling an arthropod pest which comprises applying an effective amount of the nitrile compound according to any one of the above (1) to (9) to the arthropod pest or a habitat of the arthropod pest.

The compound of the present invention has an excellent control effect on arthropod pests, and therefore it is useful as an active ingredient of a pesticidal composition.

BEST MODE FOR CARRYING OUT THE INVENTION

As used herein, the "fluoroalkyl group" means an alkyl group substituted with one or more fluorine atoms. The expression "C1-C6" or the like, as used herein, means the total number of carbon atoms constituting each substituent group.

Examples of the "C1-C4 fluoroalkyl group" represented by Q include a monofluoromethyl group, a difluoromethyl group, a trifluoromethyl group, a 1,1-difluoroethyl group, a 2,2-difluoroethyl group, a 1,2,2-trifluoroethyl group, a 2,2,2-trifluoroethyl group, a 1,1,2,2-tetrafluoroethyl group, a 1,1,2,2,2-pentafluoroethyl group, a 1-fluoropropyl group, a 2-fluoropropyl group, a 3-fluoropropyl group, a 1,1-difluoropropyl group, a 2,2-difluoropropyl group, a 3,3-difluoropropyl group, a 2,3,3-trifluoropropyl group, a 3,3,3-trifluoropropyl group, a 2,2,3,3-tetrafluoropropyl group, a 2,2,3,3,3-pentafluoropropyl group, a 1,1,2,3,3,3-hexafluoropropyl group, a 1,1,2,2,3,3,3-heptafluoropropyl group, a 2,3,3,3-tetrafluoro-2-(trifluoromethyl)propyl group, a 4-fluorobutyl group, a 2-fluorobutyl group, a 2,2-difluorobutyl group, a 3-fluorobutyl group, a 3,3-difluorobutyl group, a 4,4-difluorobutyl group, a 2,2,3-trifluorobutyl group, a 2,2,3,3-tetrafluorobutyl group, a 2,2,3,4-tetrafluorobutyl group, a 3,3,4,4-tetrafluorobutyl group, a 2,2,3,4,4-pentafluorobutyl group, a 2,2,3,4,4,4-hexafluorobutyl group, a 2,2,3,3,4,4-hexafluorobutyl group, a 2,2,3,3,4,4,4-heptafluorobutyl group, and a 1,1,2,2,3,3,4,4-octafluorobutyl group.

In the formula (I), Z together with the ring may form a single bond (Z—CH) or a double bond (Z=CH).

The group L consists of a hydroxyl group, a C1-C4 alkoxy group optionally substituted with a halogen atom, C3-C6 alkenyloxy group optionally substituted with a halogen atom, a C3-C6 alkynyloxy group optionally substituted with a halogen atom, —N($R^9$) R''', a C2-C5 cyclic amino group, —C(=O)$R^7$, —OC(=O)$R^8$, and a halogen atom. Specific examples of each member of the group L will be described below.

Examples of the "C2-C6 alkynyl group optionally substituted with a group selected from the group L" represented by Z include a 1-ethynyl group, a 2-bromoethynyl group, a 2-iodoethynyl group, a 2-(methoxycarbonyl)ethynyl group, a 1-propynyl group, a 3-fluoro-1-propynyl group, a 3,3-difluoro-1-propynyl group, a 3-(dimethylamino)-1-propynyl group, a 3,3,3-trifluoro-1-propynyl group, a 3-methoxy-1-propynyl group, a 3-methoxy-1-butynyl group, a 4-methoxy-1-butynyl group, a 4-methoxy-2-butynyl group, a 3-methoxy-1-pentynyl group, a 4-methoxy-1-pentynyl group, a 5-methoxy-1-pentynyl group, a 4-methoxy-2-pentynyl group, a 5-methoxy-2-pentynyl group, a 5-methoxy-3-pentynyl group, a 3-hydroxy-1-propynyl group, a 3-hydroxy-1-butynyl group, a 4-hydroxy-1-butynyl group, a 4-hydroxy-2-butynyl group, a 3-hydroxy-1-pentynyl group, a 4-hydroxy-1-pentynyl group, a 5-hydroxy-1-pentynyl group, a 4-hydroxy-2-pentynyl group, a 5-hydroxy-2-pentynyl group, a 5-hydroxy-3-pentynyl group, a 3-methylamino-1-propynyl group, a 3-methylamino-1-butynyl group, a 4-methylamino-1-butynyl group, a 4-methylamino-2-butynyl group, a 3-methylamino-1-pentynyl group, a 4-methylamino-1-pentynyl group, a 5-methylamino-1-pentynyl group, a 4-methylamino-2-pentynyl group, a 5-methylamino-2-pentynyl group, a 5-methylamino-3-pentynyl group, a 3-dimethylamino-1-propynyl group, a 3-dimethylamino-1-butynyl group, a 4-dimethylamino-1-butynyl group, a 4-dimethylamino-2-butynyl group, a 3-dimethylamino-1-pentynyl group, a 4-dimethylamino-1-pentynyl group, a 5-dimethylamino-1-pentynyl group, a 4-dimethylamino-2-pentynyl group, a 5-dimethylamino-2-pentynyl group, a 5-dimethylamino-3-pentynyl group, a 3-phenylamino-1-propynyl group, a 3-phenylamino-1-butynyl group, a 4-phenylamino-1-butynyl group, a 4-phenylamino-2-butynyl group, a 3-phenylamino-1-pentynyl group, a 4-phenylamino-1-pentynyl group, a 5-phenylamino-1-pentynyl group, a 4-phenylamino-2-pentynyl group, a 5-phenylamino-2-pentynyl group, a 5-phenylamino-3-pentynyl group, a 3-methylphenylamino-1-propynyl group, a 3-methylphenylamino-1-butynyl group, a 4-methylphenylamino-1-butynyl group, a 4-methylphenylamino-2-butynyl group, a 3-methylphenylamino-1-pentynyl group, a 4-methylphenylamino-1-pentynyl group, a 5-methylphenylamino-1-pentynyl group, a 4-methylphenylamino-2-pentynyl group, a 5-methylphenylamino-2-pentynyl group, a 5-methylphenylamino-3-pentynyl group, 3-(1-pyrrolidinyl)-1-propynyl group, a 3-(1-pyrrolidinyl)-1-butynyl group, a 4-(1-pyrrolidinyl)-1-butynyl group, a 4-(1-pyrrolidinyl)-2-butynyl group, a 3-(1-pyrrolidinyl)-1-pentynyl group, a 4-(1-pyrrolidinyl)-1-pentynyl group, a 5-(1-pyrrolidinyl)-1-pentynyl group, a 4-(1-pyrrolidinyl)-2-pentynyl group, a 5-(1-pyrrolidinyl)-2-pentynyl group, a 5-(1-pyrrolidinyl)-3-pentynyl group, a 3-(1-piperidinyl)-1-propynyl group, a 3-(1-piperidinyl)-1-butynyl group, a 4-(1-piperidinyl)-1-butynyl group, a 4-(1-piperidinyl)-2-butynyl group, a 3-(1-piperidinyl)-1-pentynyl group, a 4-(1-piperidinyl)-1-pentynyl group, a 5-(1-piperidinyl)-1-pentynyl group, a 4-(1-piperidinyl)-2-pentynyl group, a 5-(1-piperidinyl)-2-pentynyl group, a 5-(1-piperidinyl)-3-pentynyl group, a 3-(1-morpholinyl)-1-propynyl group, a 3-(1-morpholinyl)-1-butynyl group, a 4-(1-morpholinyl)-1-butynyl group, a 4-(1-morpholinyl)-2-butynyl group, a 3-(1-morpholinyl)-1-pentynyl group, a 4-(1-morpholinyl)-1-pentynyl group, a 5-(1-morpholinyl)-1-pentynyl group, a 4-(1-morpholinyl)-2-pentynyl group, a 5-(1-morpholinyl)-2-pentynyl group, a 5-(1-morpholinyl)-3-pentynyl group, a 3-methoxycarbonyl-1-propynyl group, a 3-methoxycarbonyl-1-butynyl group, a 4-methoxycarbonyl-1-butynyl group, a 4-methoxycarbonyl-2-butynyl group, a 3-methoxycarbonyl-1-pentynyl group, a 4-methoxycarbonyl-1-pentynyl group, a 5-methoxycarbonyl-1-pentynyl group, a 4-methoxycarbonyl-2-pentynyl group, a 5-methoxycarbonyl-2-pentynyl group, a 5-methoxycarbonyl-3-pentynyl group, a 3-dimethylaminocarbonyl-1-propynyl group, 3-dimethylaminocarbonyl-1-butynyl group, a 4-dimethylaminocarbonyl-1-butynyl group, a 4-dimethylaminocarbonyl-2-butynyl group, a 3-dimethylaminocarbonyl-1-pentynyl group, a 4-dimethylaminocarbonyl-1-pentynyl group, a 5-dimethylaminocarbonyl-1-pentynyl group, a 4-dimethylaminocarbonyl-2-pentynyl group, a 5-dimethylaminocarbonyl-2-pentynyl group, a 5-dimethylaminocarbonyl-3-pentynyl group, a 3-(1-pyrrolidinyl)carbonyl-1-propynyl group, a 3-(1-pyrrolidinyl)carbonyl-1-butynyl group, a 4-(1-pyrrolidinyl)carbonyl-1-butynyl group, a 4-(1-pyrrolidinyl)carbonyl-2-butynyl group, a 3-(1-pyrrolidinyl)carbonyl-1-pentynyl group, a 4-(1-pyrrolidinyl)carbonyl-1-pentynyl group, a 5-(1-pyrrolidinyl)carbonyl-1-pentynyl group, a 4-(1-pyrrolidinyl)carbonyl-2-pentynyl group, a 5-(1-pyrrolidinyl)carbonyl-2-pentynyl group, a 5-(1-pyrrolidinyl)carbonyl-3-pentynyl group, a 3-(1-piperidinyl)carbonyl-1-propynyl group, a 3-(1-piperidinyl)carbonyl-1-butynyl group, a 4-(1-piperidinyl)carbonyl-1-butynyl group, a 4-(1-piperidinyl)carbonyl-2-butynyl group, a 3-(1-piperidinyl)carbonyl-1-pentynyl group, a 4-(1-piperidinyl)carbonyl-1-pentynyl group, a 5-(1- piperidinyl)carbonyl-1-pentynyl group, a 4-(1-piperidinyl)carbonyl-2-pentynyl group, a 5-(1-piperidinyl)carbonyl-2-pentynyl group, a 5-(1-piperidinyl)carbonyl-3-pentynyl group, a 3-(1-morpholinyl)carbonyl-1-propynyl group, a 3-(1-morpholinyl)carbonyl-1-butynyl group, a 4-(1-morpholinyl)carbonyl-1-butynyl group, a 4-(1-morpholinyl)carbonyl-2-butynyl group, a 3-(1-morpholinyl)carbonyl-1-pentynyl group, a 4-(1-morpholinyl)carbonyl-1-pentynyl group, a 5-(1-morpholinyl)carbonyl-1-pentynyl group, a 4-(1-morpholinyl)carbonyl-2-pentynyl group, a 5-(1-morpholinyl)carbonyl-2-pentynyl group, a 5-(1-morpholinyl)carbonyl-3-pentynyl group, a 3-carboxy-1-propynyl group, a 3-carboxy-1-butynyl group, a 4-carboxy-1-butynyl group, a 4-carboxy-2-butynyl group, a 3-carboxy-1-pentynyl group, a 4-carboxy-1-pentynyl group, a 5-carboxy-1-pentynyl group, a 4-carboxy-2-pentynyl group, a 5-carboxy-2-pentynyl group, a 5-carboxy-3-pentynyl group, a 3-acetoxy-1-propynyl group, a 3-acetoxy-1-butynyl group, a 4-acetoxy-1-butynyl group, a 4-acetoxy-2-butynyl group, 3-acetoxy-1-pentynyl group, a 4-acetoxy-1-pentynyl group, a 5-acetoxy-1-pentynyl group, a 4-acetoxy-2-pentynyl group, a 5-acetoxy-2-pentynyl group, a 5-acetoxy-3-pentynyl group, a 3-methoxycarbonyloxy-1-propynyl group, a 3-methoxycarbonyloxy-1-butynyl group, a 4-methoxycarbonyloxy-1-butynyl group, a 4-methoxycarbonyloxy-2-butynyl group, a 3-methoxycarbonyloxy-1-pentynyl group, a 4-methoxycarbonyloxy-1-pentynyl group, a 5-methoxycarbonyloxy-1-pentynyl group, a 4-methoxycarbonyloxy-2-pentynyl group, a 5-methoxycarbonyloxy-2-pentynyl group, a 5-methoxycarbonyloxy-3-pentynyl group, a 2-bromoethynyl group, a 2-iodoethynyl group, a 3-fluoro-1-propynyl group, a 3,3-difluoro-1-propynyl group, a 3,3,3-trifluoro-1-propynyl group, a 3-fluoro-1-propynyl group, a 3,3-difluoro-1-propynyl group, a 3,3,3-trifluoro-1-propynyl group, a 1-fluoro-2-propynyl group, a 1,1-difluoro-2-propynyl group, a 3-fluoro-1-butynyl group, a 4-fluoro-1-butynyl group, a 3-fluoro-1-pentynyl group, a 4-fluoro-1-pentynyl group, a 5-fluoro-1-pentynyl group, an ethynyl group, a 1-propynyl group, a 2-propynyl group, a 1-butynyl group, a 2-butynyl group, a 3-butynyl group, a 1-pentynyl group, a 2-pentynyl group, and a 3-pentynyl group.

Examples of the "monovalent C1-C4 chain hydrocarbon group optionally substituted with a halogen atom" represented by $R^1$ or $R^2$ include a C1-C4 alkyl group and a C1-C4 alkyl group substituted with a halogen atom, such as a methyl group, a fluoromethyl group, a difluoromethyl group, a trifluoromethyl group, an ethyl group, and propyl group; a C2-C4 alkenyl group and a C2-C4 alkenyl group substituted with a halogen atom, such as a vinyl group, a 2,2-difluorovinyl group, a 1-propenyl group, and a 2-propenyl group; and a C2-C4 alkynyl group and a C2-C4 alkynyl group substituted with a halogen atom, such as a 2-propynyl group.

Examples of the "—C(=G)$R^5$" represented by $R^1$ or $R^2$ include a methoxycarbonyl group, a methoxythiocarbonyl group, a carbamoyl group, and an N,N-dimethylcarbamoyl group.

Examples of the "monovalent C1-C6 chain hydrocarbon group optionally substituted with a group selected from the group L" represented by A include a C1-C6 alkyl group and a C1-C6 alkyl group substituted with a group selected from the group L, such as a methyl group, a fluoromethyl group, a difluoromethyl group, a trifluoromethyl group, a 2-propynyloxymethyl group, a 2-butynyloxymethyl group, and a hydroxymethyl group;
a C2-C6 alkenyl group and a C2-C6 alkenyl group substituted with a group selected from the group L, such as a vinyl group, a 2,2-difluorovinyl group, a 1-propenyl group, and a 2-propenyl group; and
a C2-C6 alkynyl group and a C2-C6 alkynyl group substituted with a group selected from the group L, such as a 1-ethynyl group, a 2-bromoethynyl group, a 2-iodoethynyl group, a 2-(methoxycarbonyl)ethynyl group, a 1-propynyl group, a 3-fluoro-1-propynyl group, a 3,3-difluoro-1-propynyl group, a 3-(dimethylamino)-1-propynyl group, 3,3,3-trifluoro-1-propynyl group, a 3-methoxy-1-propynyl group, a 3-methoxy-1-butynyl group, a 4-methoxy-1-butynyl group, a 4-methoxy-2-butynyl group, a 3-methoxy-1-pentynyl group, a 4-methoxy-1-pentynyl group, a 5-methoxy-1-pentynyl group, a 4-methoxy-2-pentynyl group, a 5-methoxy-2-pentynyl group, a 5-methoxy-3-pentynyl group, a 3-hydroxy-1-propynyl group, a 3-hydroxy-1-butynyl group, a 4-hydroxy-1-butynyl group, a 4-hydroxy-2-butynyl group, a 3-hydroxy-1-pentynyl group, a 4-hydroxy-1-pentynyl group, a 5-hydroxy-1-pentynyl group, a 4-hydroxy-2-pentynyl group, a 5-hydroxy-2-pentynyl group, a 5-hydroxy-3-pentynyl group, a 3-methylamino-1-propynyl group, a 3-methylamino-1-butynyl group, a 4-methylamino-1-butynyl group, a 4-methylamino-2-butynyl group, a 3-methylamino-1-pentynyl group, a 4-methylamino-1-pentynyl group, a 5-methylamino-1-pentynyl group, a 4-methylamino-2-pentynyl group, a 5-methylamino-2-pentynyl group, a 5-methylamino-3-pentynyl group, a 3-dimethylamino-1-propynyl group, a 3-dimethylamino-1-butynyl group, a 4-dimethylamino-1-butynyl group, a 4-dimethylamino-2-butynyl group, a 3-dimethylamino-1-pentynyl group, a 4-dimethylamino-1-pentynyl group, a 5-dimethylamino-1-pentynyl group, a 4-dimethylamino-2-pentynyl group, a 5-dimethylamino-2-pentynyl group, a 5-dimethylamino-3-pentynyl group, a 3-phenylamino-1-propynyl group, a 3-phenylamino-1-butynyl group, a 4-phenylamino-1-butynyl group, a 4-phenylamino-2-butynyl group, a 3-phenylamino-1-pentynyl group, a 4-phenylamino-1-pentynyl group, a 5-phenylamino-1-pentynyl group, a 4-phenylamino-2-pentynyl group, a 5-phenylamino-2-pentynyl group, a 5-phenylamino-3-pentynyl group, a 3-methylphenylamino-1-propynyl group, a 3-methylphenylamino-1-butynyl group, a 4-methylphenylamino-1-butynyl group, a 4-methylphenylamino-2-butynyl group, a 3-methylphenylamino-1-pentynyl group, a 4-methylphenylamino-1-pentynyl group, a 5-methylphenylamino-1-pentynyl group, a 4-methylphenylamino-2-pentynyl group, 5-methylphenylamino-2-pentynyl group, a 5-methylphenylamino-3-pentynyl group, a 3-(1-pyrrolidinyl)-1-propynyl group, a 3-(1-pyrrolidinyl)-1-butynyl group, a 4-(1-pyrrolidinyl)-1-butynyl group, a 4-(1-pyrrolidinyl)-2-butynyl group, a 3-(1-pyrrolidinyl)-1-pentynyl group, a 4-(1-pyrrolidinyl)-1-pentynyl group, a 5-(1-pyrrolidinyl)-1-pentynyl group, a 4-(1-pyrrolidinyl)-2-pentynyl group, a 5-(1-pyrrolidinyl)-2-pentynyl group, a 5-(1-pyrrolidinyl)-3-pentynyl group, a 3-(1-piperidinyl)-1-propynyl group, a 3-(1-piperidinyl)-1-butynyl group, a 4-(1-piperidinyl)-1-butynyl group, a 4-(1-piperidinyl)-2-butynyl group, a 3-(1-piperidinyl)-1-pentynyl group, a 4-(1-piperidinyl)-1-pentynyl group, a 5-(1-piperidinyl)-1-pentynyl group, a 4-(1-piperidinyl)-2-pentynyl group, a 5-(1-piperidinyl)-2-pentynyl group, a 5-(1-piperidinyl)-3-pentynyl group, a 3-(1-morpholinyl)-1-propynyl group, a 3-(1-morpholinyl)-1-butynyl group, a 4-(1-morpholinyl)-1-butynyl group, a 4-(1-morpholinyl)-2-butynyl group, a 3-(1-morpholinyl)-1-pentynyl group, a 4-(1-morpholinyl)-1-pentynyl group, a 5-(1-morpholinyl)-1-pentynyl group, a 4-(1-morpholinyl)-2-pentynyl group, a 5-(1-morpholinyl)-2-pentynyl group, a 5-(1-morpholinyl)-3-pentynyl group, a 3-methoxycarbonyl-1-propynyl group, a 3-methoxycarbonyl-1-butynyl group, a 4-methoxycarbonyl-1-butynyl group, a 4-methoxycarbonyl-2-butynyl group, a 3-methoxycarbonyl-1-pentynyl group, a 4-methoxycarbonyl-1-pentynyl group, a 5-methoxycarbonyl-1-pentynyl group, a 4-methoxycarbonyl-2-pentynyl group, a 5-methoxycarbonyl-2-pentynyl group, a 5-methoxycarbonyl-3-pentynyl group, a 3-dimethylaminocarbonyl-1-propynyl group, a 3-dimethylaminocarbonyl-1-butynyl group, a 4-dimethylaminocarbonyl-1-butynyl group, a 4-dimethylaminocarbonyl-2-butynyl group, a 3-dimethylaminocarbonyl-1-pentynyl group, a 4-dimethylaminocarbonyl-1-pentynyl group, a 5-dimethylaminocarbonyl-1-pentynyl group, a 4-dimethylaminocarbonyl-2-pentynyl group, a 5-dimethylaminocarbonyl-2-pentynyl group, a 5-dimethylaminocarbonyl-3-pentynyl group, a 3-(1-pyrrolidinyl)carbonyl-1-propynyl group, a 3-(1-pyrrolidinyl)carbonyl-1-butynyl group, a 4-(1-pyrrolidinyl)carbonyl-1-butynyl group, a 4-(1-pyrrolidinyl)carbonyl-2-butynyl group, a 3-(1-pyrrolidinyl)carbonyl-1-pentynyl group, a 4-(1-pyrrolidinyl)carbonyl-1-pentynyl group, a 5-(1-pyrrolidinyl)carbonyl-1-pentynyl group, a 4-(1-pyrrolidinyl)carbonyl-2-pentynyl group, a 5-(1-pyrrolidinyl)carbonyl-2-pentynyl group, a 5-(1-pyrrolidinyl)carbonyl-3-pentynyl group, a 3-(1-piperidinyl)carbonyl-1-propynyl group, a 3-(1-piperidinyl)carbonyl-1-butynyl group, a 4-(1-piperidinyl)carbonyl-1-butynyl group, a 4-(1-piperidinyl)carbonyl-2-butynyl group, a 3-(1-piperidinyl)carbonyl-1-pentynyl group, a 4-(1-piperidinyl)carbonyl-1-pentynyl group, a 5-(1-piperidinyl)carbonyl-1-pentynyl group, a 4-(1-piperidinyl)carbonyl-2-pentynyl group, a 5-(1-piperidinyl)carbonyl-2-pentynyl group, a 5-(1-piperidinyl)carbonyl-3-pentynyl group, a 3-(1-morpholinyl)carbonyl-1-propynyl group, a 3-(1-morpholinyl)carbonyl-1-butynyl group, a 4-(1-morpholinyl)carbonyl-1-butynyl group, a 4-(1-morpholinyl)carbonyl-2-butynyl group, a 3-(1-morpholinyl)carbonyl-1-pentynyl group, a 4-(1-morpholinyl)carbonyl-1-pentynyl group, a 5-(1-morpholinyl)carbonyl-1-pentynyl group, a 4-(1-morpholinyl)carbonyl-2-pentynyl group, a 5-(1-morpholinyl)carbonyl-2-pentynyl group, a 5-(1-morpholinyl)carbonyl-3-pentynyl group, a 3-carboxy-1-propynyl group, a 3-carboxy-1-butynyl group, a 4-carboxy-1-butynyl group, a 4-carboxy-2-butynyl group, a 3-carboxy-1-pentynyl group, a 4-carboxy-1-pentynyl group, a 5-carboxy-1-pentynyl group, a 4-carboxy-2-pentynyl group, a 5-carboxy-2-pentynyl group, a 5-carboxy-3-pentynyl group, a 3-acetoxy-1-propynyl group, a 3-acetoxy-1-butynyl group, a 4-acetoxy-1-butynyl group, a 4-acetoxy-2-butynyl group, a 3-acetoxy-1-pentynyl group, a 4-acetoxy-1-pentynyl group, a 5-acetoxy-1-pentynyl group, a 4-acetoxy-2-pentynyl group, a 5-acetoxy-2-pentynyl group, a 5-acetoxy-3-pentynyl group, a 3-methoxycarbonyloxy-1-propynyl group, a 3-methoxycarbonyloxy-1-butynyl group, a 4-methoxycarbonyloxy-1-butynyl group, a 4-methoxycarbonyloxy-2-butynyl group, a 3-methoxycarbonyloxy-1-pentynyl group, a 4-methoxycarbonyloxy-1-pentynyl group, a 5-methoxycarbonyloxy-1-pentynyl group, a 4-methoxycarbonyloxy-2-pentynyl group, a 5-methoxycarbonyloxy-2-pentynyl group, a 5-methoxycarbonyloxy-3-pentynyl group, a 2-bromoethynyl group, a 2-iodoethynyl group, a 3-fluoro-1-propynyl group, a 3,3-difluoro-1-propynyl group, a 3,3,3-trifluoro-1-propynyl group, a 3-fluoro-1-propynyl group, a 3,3-difluoro-1-propynyl group, a 3,3,3-trifluoro-1-propynyl group, a 1-fluoro-2-propynyl group, a 1,1-difluoro-2-propynyl group, a 3-fluoro-1-butynyl group, a 4-fluoro-1-butynyl group, a 3-fluoro-1-pentynyl group, a 4-fluoro-1-pentynyl group, a 5-fluoro-1-pentynyl group, an ethynyl group, a 1-propynyl group, a 2-propynyl group, a 1-butynyl group, a 2-butynyl group, a 3-butynyl group, a 1-pentynyl group, a 2-pentynyl group, and a 3-pentynyl group.

Examples of the "C3-C6 cycloalkyl group optionally substituted with a halogen atom" include a cyclopropyl group, a difluorocyclopropyl group, a dichlorocyclopropyl group, and a dibromocyclopropyl group.

Examples of a group represented by "—$OR^6$" include a C1-C4 alkoxy group and a C1-C4 alkoxy group substituted with a halogen atom, such as a 2-propynyloxy group and a 2-butynyloxy group, a cycloalkyl group, and a cycloalkyl group substituted with a halogen atom.

Examples of a group represented by "—$SR^6$" include a C1-C4 alkylthio group and a C1-C4 alkylthio group substituted with a halogen atom, such as a methylthio group and a trifluoromethylthio group.

Examples of a group represented by "—$S(=O)R^6$" include a C1-C4 alkylsulfinyl group, such as a methylsulfinyl group and a trifluoromethylsulfinyl group.

Examples of a group represented by "—$S(=O)_2R^6$" include a C1-C4 alkylsulfonyl group and a C1-C4 alkylsulfonyl group substituted with a halogen atom, such as a methylsulfonyl group and a trifluoromethylsulfonyl group.

Examples of $R^7$ of the "—$C(=O)R^7$" include a C1-C4 alkyl group and a C1-C4 alkyl group substituted with a halogen atom; a C1-C4 alkoxy group and a C1-C4 alkoxy group substituted with a halogen atom; a C3-C6 alkenyloxy group and a C3-C6 alkenyloxy group substituted with a halogen atom; a C3-C6 alkynyloxy group and a C3-C6 alkynyloxy group substituted with a halogen atom; an amino group; a C1-C4 alkylamino group and a C1-C4 alkylamino group substituted with a halogen atom; a di(C1-C4 alkyl)amino group and a di(C1-C4 alkyl)amino group substituted with a halogen atom; a C2-C5 cyclic amino group; a hydroxyl group; and a hydrogen atom.

Examples of $R^8$ of the "—$OC(=O)R^8$" include a C1-C4 alkyl group and a C1-C4 alkyl group substituted with a halogen atom; a C1-C4 alkoxy group and a C1-C4 alkoxy group substituted with a halogen atom; a C3-C6 alkenyloxy group and a C3-C6 alkenyloxy group substituted with a halogen atom; a C3-C6 alkynyloxy group and a C3-C6 alkynyloxy group substituted with a halogen atom; an amino group; a C1-C4 alkylamino group and a C1-C4 alkylamino group substituted with a halogen atom; a di(C1-C4 alkyl)amino group and a di(C1-C4 alkyl)amino group substituted with a halogen atom; a C2-C5 cyclic amino group; a hydroxyl group; and a hydrogen atom.

Examples of the "C2-C6 alkanediyl group optionally substituted with a group selected from the group L" include an ethane-1,2-diyl group, a propane-1,2-diyl group, a propane-1,3-diyl group, a butane-1,4-diyl group, a 2,3-dichlorobutane-1,4-diyl group, and a pentane-1,5-diyl group.

Examples of the "C4-C6 alkenediyl group optionally substituted with a group selected from the group L" include a 2-butene-1,4-diyl group and a 3-pentene-1,5-diyl group.

Examples of the "C2-C6 alkanediyl group" represented by $T^1$ or $T^2$ include an ethane-1,2-diyl group, a propane-1,2-diyl group, a propane-1,3-diyl group, a butane-1,4-diyl group, and a pentane-1,5-diyl group.

Examples of a group represented by the "-G-$T^1$-G-" include —$OCH_2O$—, —$SCH_2S$—, —$OCH_2CH_2O$— and —$SCH_2CH_2S$—.

Examples of a group represented by the "-G-$T^1$-G-$T^2$-" include —$OCH_2OCH_2$—, —$SCH_2SCH_2$—, —$OCH_2CH_2OCH_2$— and —$SCH_2CH_2SCH_2$—.

Examples of the "monovalent C1-C6 chain hydrocarbon group optionally substituted with a halogen atom" represented by $R^3$ include a C1-C6 alkyl group and a C1-C6 alkyl group substituted with a halogen atom, such as a methyl group, a fluoromethyl group, a difluoromethyl group, a trifluoromethyl group, an ethyl group, a propyl group, an isopropyl group and a 1,1-dimethylethyl group;

a C3-C6 alkenyl group and a C3-C6 alkenyl group substituted with a halogen atom, such as a 2-propenyl group and a 3,3-dichloro-2-propenyl group; and a C3-C6 alkynyl group and a C3-C6 alkynyl group substituted with a halogen atom, such as a 2-propynyl group.

Examples of the "C1-C4 alkyl group" represented by $R^4$ include a methyl group, an ethyl group, and a propyl group.

Examples of the "C1-C4 alkyl group optionally substituted with a halogen atom" represented by $R^5$, $R^6$, $R^7$, $R^8$, $R^9$ or $R^{10}$ or as a member of the group L (hereinafter these groups are sometimes collectively referred to as "substituents $R^5$ or others") include a methyl group, an ethyl group, a propyl group, a 1-methylethyl group (hereinafter may be referred to as an i-propyl group), a 2,2-dimethylpropyl group, a chloromethyl group, a fluoromethyl group, a difluoromethyl group, a trifluoromethyl group, a 2,2,2-trifluoroethyl group, a 1,1,2,2-tetrafluoroethyl group, a 1,1,2,2,2-pentafluoroethyl group, and a 1,1-dimethylethyl group (hereinafter may be referred to as a t-butyl group).

Examples of the "C1-C4 alkoxy group optionally substituted with a halogen atom" represented by the substituents $R^5$ or others include a methoxy group, an ethoxy group, a propoxy group, a trifluoromethoxy group, a bromodifluoromethoxy group, a difluoromethoxy group, a chlorodifluoromethoxy group, a pentafluoroethoxy group, a 2,2,2-trifluoroethoxy group, and a 1,1,2,2-tetrafluoroethoxy group.

Examples of the "C3-C6 alkenyloxy group optionally substituted with a halogen atom" represented by the substituents $R^5$ or others include a 1-propenyloxy group, a 2-propenyloxy group, a 1-methyl-2-propenyloxy group, a 1,1-dimethyl-2-propenyloxy group, and a 2,2-difluoro-2-propenyloxy group.

Examples of the "C3-C6 alkynyloxy group optionally substituted with a halogen atom" represented by the substituents $R^5$ or others include a 2-propynyloxy group, a 1-methyl-2-propynyloxy group, a 1,1-dimethyl-2-propynyloxy group, a 2-butynyloxy group, a 1-methyl-2-butynyloxy group, a 1,1-dimethyl-2-butynyloxy group, and a 3,3,3-trifluoro-1-propynyloxy group.

Examples of the "C1-C4 alkylamino group optionally substituted with a halogen atom" represented by the substituents $R^5$ or others include an N-methylamino group, an N-ethylamino group, an N-propylamino group, an N-(1-methylethyl)amino group, and an N-(2,2,2-trifluoroethyl)amino group.

Examples of the "di(C1-C4 alkyl)amino group optionally substituted with a halogen atom" represented by the substituents $R^5$ or others include an N,N-dimethylamino group, an N-ethyl-N-methylamino group, an N,N-diethylamino group, an N-methyl-N-propylamino group, an N-ethyl-N-propylamino group, an N,N-dipropylamino group, an N-methyl-N-(1-methylethyl)amino group, an N-ethyl-N-(1-methylethyl)amino group, an N,N-di(1-methylethyl)amino group, an N-methyl-N-(2,2,2-trifluoroethyl)amino group, and an N-methyl-N-ethyl-N-(2,2,2-trifluoroethyl)amino group.

Examples of the "C2-C5 cyclic amino group" represented by the substituents $R^5$ or others include a 1-aziridino group, a 1-azetidinyl group, a 1-pyrrolidinyl group, a piperidino group, and a morpholino group.

Examples of the "C3-C6 cycloalkyl group optionally substituted with a halogen atom" represented by the substituents $R^5$ or others include a cyclopropyl group, a 1-methylcyclopropyl group, a 2,2-dichlorocyclopropyl group, a 2,2-dichloro-1-methylcyclopropyl group, a 2,2-difluorocyclopropyl group, a 2,2-difluoro-1-methylcyclopropyl group, a cyclobutyl group, a cyclopentyl group, and a cyclohexyl group.

Examples of the "phenyl group optionally substituted with a halogen atom" represented by the substituents $R^5$ or others include a phenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2-bromophenyl group, a 3-bromophenyl group, a 4-bromophenyl group, a 2,3-dibromophenyl group, a 2,4-dibromophenyl group, a 2,5-dibromophenyl group, a 2,6-dibromophenyl group, a 3,4-dibromophenyl group, and a 3,5-dibromophenyl group.

The compound of the present invention has an asymmetric carbon atom. The present invention includes all isomers, racemate, and mixtures of isomers at optional ratios all of which have the activity.

Specific examples of the compound of the present invention include:

a compound of the formula (I), wherein n is 0;
a compound of the formula (I), wherein n is 1;
a compound of the formula (I), wherein n is 2;
a compound of the formula (I), wherein $R^1$ is a hydrogen atom;
a compound of the formula (I), wherein $R^1$ is a C1-C4 alkyl group optionally substituted with a halogen atom;
a compound of the formula (I), wherein $R^1$ is a methyl group;
a compound of the formula (I), wherein $R^1$ is a C2-C4 alkenyl group optionally substituted with a halogen atom;
a compound of the formula (I), wherein $R^1$ is a C2-C4 alkynyl group optionally substituted with a halogen atom;
a compound of the formula (I), wherein $R^1$ is a halogen atom;
a compound of the formula (I), wherein $R^1$ is a fluorine atom;
a compound of the formula (I), wherein $R^1$ is a chlorine atom;
a compound of the formula (I), wherein $R^1$ is a bromine atom;
a compound of the formula (I), wherein $R^2$ is a hydrogen atom;
a compound of the formula (I), wherein $R^2$ is a C1-C4 alkyl group optionally substituted with a halogen atom;
a compound of the formula (I), wherein $R^2$ is a group represented by —C(=O)$R^5$, and $R^5$ is a C1-C4 alkyl group optionally substituted with a halogen atom;
a compound of the formula (I), wherein $R^2$ is a group represented by —C(=O)$R^5$, and $R^5$ is a C1-C4 alkoxy group optionally substituted with a halogen atom;
a compound of the formula (I), wherein $R^2$ is a methoxycarbonyl group;
a compound of the formula (I), wherein $R^2$ is a group represented by —C(=O)$R^5$, and $R^5$ is a C3-C6 alkenyloxy group optionally substituted with a halogen atom;
a compound of the formula (I), wherein $R^2$ is a group represented by —C(=O)$R^5$ and $R^5$ is a C3-C6 alkynyloxy group optionally substituted with a halogen atom;
a compound of the formula (I), wherein $R^2$ is a group represented by —C(=O)$R^5$, and $R^5$ is an amino group, a C1-C4 alkylamino group optionally substituted with a halogen atom or a di(C1-C4 alkyl)amino group optionally substituted with a halogen atom;
a compound of the formula (I), wherein $R^2$ is a group represented by —C(=O)$R^5$, and $R^5$ is a C2-C5 cyclic amino group;

a compound of the formula (I), wherein $R^2$ is —C(=O)NH$_2$;
a compound of the formula (I), wherein $R^2$ is —C(=O)OH;
a compound of the formula (I), wherein $R^2$ is —C(=O)H;
a compound of the formula (I), wherein $R^2$ is a group represented by —C(=S)$R^5$, and $R^5$ is a C1-C4 alkyl group optionally substituted with a halogen;
a compound of the formula (I), wherein $R^2$ is a group represented by —C(=S)$R^5$, and $R^5$ is a C1-C4 alkoxy group optionally substituted with a halogen;
a compound of the formula (I), wherein $R^2$ is a group represented by —C(=S)$R^5$, and $R^5$ is a C3-C6 alkenyloxy group optionally substituted with a halogen atom;
a compound of the formula (I), wherein $R^2$ is a group represented by —C(=S)$R^5$ and $R^5$ is a C3-C6 alkynyloxy group optionally substituted with a halogen atom;
a compound of the formula (I), wherein $R^2$ is a group represented by —C(=S)$R^5$, and $R^5$ is a C1-C4 alkylamino group optionally substituted with a halogen atom or a di(C1-C4 alkyl)amino group optionally substituted with a halogen atom;
a compound of the formula (I), wherein $R^2$ is a group represented by —C(=S)$R^5$, and $R^5$ is a C2-C5 cyclic amino group;
a compound of the formula (I), wherein $R^2$ is —C(=S)NH$_2$;
a compound of the formula (I), wherein $R^2$ is a group represented by —C(=S)$R^5$, and $R^5$ is a hydroxyl group;
a compound of the formula (I), wherein $R^2$ is —C(=S)H;
a compound of the formula (I), wherein $R^2$ is a cyano group;
a compound of the formula (I), wherein $R^2$ is a halogen atom;
a compound of the formula (I), wherein $R^1$ and $R^2$ are hydrogen atoms;
a compound of the formula (I), wherein n is 1, and $R^1$ and $R^2$ are hydrogen atoms;
a compound of the formula (I), wherein Q is a C1-C3 fluoroalkyl group;
a compound of the formula (I), wherein Q is a fluoromethyl group;
a compound of the formula (I), wherein Q is a trifluoroethyl group;
a compound of the formula (I), wherein Q is a 2,2,2-trifluoroethyl group;
a compound of the formula (I), wherein Q is a 1,1,2,2,2-pentafluoroethyl group;
a compound of the formula (I), wherein Z is a C2-C5 alkynyl group optionally substituted with a group selected from the group L;
a compound of the formula (I), wherein Z is a =N—O$R^3$ group, and $R^3$ is a monovalent C1-C6 chain hydrocarbon group;
a compound of the formula (I), wherein Z is a —C≡C—$R^4$ group, and $R^4$ is a C1-C4 alkyl group or a hydrogen atom;
a compound of the formula (I), wherein Z is a 1-ethynyl group;
a compound of the formula (I), wherein Z is a 1-propynyl group;
a compound of the formula (I), wherein Z is a 3-fluoro-1-propynyl group;
a compound of the formula (I), wherein Z is a 2-propynyl group;
a compound of the formula (I), wherein Z is a 1-fluoro-2-propynyl group;
a compound of the formula (I), wherein Z is a 3-(dimethylamino)-1-propynyl group;
a compound of the formula (I), wherein Z is a 3-methoxy-1-propynyl group;
a compound of the formula (I), wherein Z is a 1-butynyl group;
a compound of the formula (I), wherein Z is a 4-(methoxycarbonyl)-1-butynyl group;
a compound of the formula (I), wherein Z is a =N—O$R^3$ group, and $R^3$ is a monovalent C1-C6 chain hydrocarbon group optionally substituted with a halogen atom, or a hydrogen atom;
a compound of the formula (I), wherein Z is a =N—O$R^3$ group, and $R^3$ is a monovalent C1-C6 chain hydrocarbon group;
a compound of the formula (I), wherein Z is a methoxyimino group;
a compound of the formula (I), wherein Z is a (1,1-dimethylethoxy)imino group;
a compound of the formula (I), wherein Z is a (2-propenyloxy)imino group;
a compound of the formula (I), wherein A is a monovalent C1-C6 chain hydrocarbon group optionally substituted with a group selected from the group L (wherein the group L is as defined above);
a compound of the formula (I), wherein A is a C1-C6 alkyl group optionally substituted with a group selected from the group L (wherein the group L is as defined above);
a compound of the formula (I), wherein A is a monovalent C2-C6 alkenyl group optionally substituted with a group selected from the group L (wherein the group L is as defined above);
a compound of the formula (I), wherein A is a C2-C6 alkynyl group optionally substituted with a group selected from the group L (wherein the group L is as defined above);
a compound of the formula (I), wherein A is a C3-C6 cycloalkyl group optionally substituted with a halogen atom;
a compound of the formula (I), wherein A is a group represented by "—O$R^6$" (wherein $R^6$ is as defined above);
a compound of the formula (I), wherein A is a group represented by "—S$R^6$" (wherein $R^6$ is as defined above);
a compound of the formula (I), wherein A is a group represented by "—S(=O)$R^6$" (wherein $R^6$ is as defined above);
a compound of the formula (I), wherein A is a group represented by "—S(=O)$_2$$R^6$" (wherein $R^6$ is as defined above);
a compound of the formula (I), wherein A is a group represented by "—C(=O)$R^7$" (wherein $R^7$ is as defined above);
a compound of the formula (I), wherein A is a group represented by "—OC(=O)$R^8$" (wherein $R^8$ is as defined above);
a compound of the formula (I), wherein q is 2, and two A's optionally form together a C2-C6 alkanediyl group optionally substituted with a group selected from the group L;
a compound of the formula (I), wherein q is 2, and two A's optionally form together a C4-C6 alkenediyl group optionally substituted with a group selected from the group L;
a compound of the formula (I), wherein q is 2, and two A's optionally form together a group represented by -G-$T^1$-G- (wherein G and $T^1$ are as defined above);
a compound of the formula (I), wherein q is 2, and two A's optionally form together a group represented by -G-$T^1$-G-$T^2$- (wherein G, $T^1$ and $T^2$ are as defined above);
a compound of the formula (I), wherein A is a halogen atom;
a compound of the formula (I), wherein A is a fluorine atom;
a compound of the formula (I), wherein A is a chlorine atom;
a compound of the formula (I), wherein A is a hydroxyl group;
a compound of the formula (I), wherein A is a cyano group;
a compound of the formula (I), wherein m is 0;
a compound of the formula (I), wherein m is 1;
a compound of the formula (I), wherein m is 2;
a compound of the formula (I), wherein m is 3;
a compound of the formula (I), wherein m is 4; and
a compound of the formula (I), wherein $R^1$ and $R^2$ are hydrogen atoms, n is 1 or 2, q is an integer of 0 to 2, Z is a C2-C4 alkynyl group or =N—OR³, R³ is a C1-C4 alkyl group or C2-C4 alkenyl group, and A is a halogen atom or hydroxyl group, or two A's form together —O—.

The compound of the present invention includes a compound of the formula (Ia):

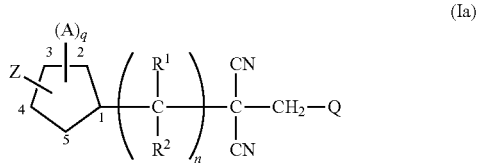

wherein A, n, q, Q, R¹, R² and Z are as defined above. Further, specific examples of the compound of the present invention include:

a compound of the formula (Ia), wherein Z is a 1-ethynyl group;
a compound of the formula (Ia), wherein Z is a 1-propynyl group;
a compound of the formula (Ia), wherein Z is a 3-fluoro-1-propynyl group;
a compound of the formula (Ia), wherein Z is a 2-propynyl group;
a compound of the formula (Ia), wherein Z is a 1-fluoro-2-propynyl group;
a compound of the formula (Ia), wherein Z is a 3-(dimethylamino)-1-propynyl group;
a compound of the formula (Ia), wherein Z is a 3-methoxy-1-propynyl group;
a compound of the formula (Ia), wherein Z is a 1-butynyl group;
a compound of the formula (Ia), wherein Z is a 4-(methoxycarbonyl)-1-butynyl group;
a compound of the formula (Ia), wherein n is 1, and Z is a 1-ethynyl group;
a compound of the formula (Ia), wherein n is 1, and Z is a 1-propynyl group;
a compound of the formula (Ia), wherein n is 1, and Z is a 3-fluoro-1-propynyl group;
a compound of the formula (Ia), wherein n is 1, and Z is a 2-propynyl group;
a compound of the formula (Ia), wherein n is 1, and Z is a 1-fluoro-2-propynyl group;
a compound of the formula (Ia), wherein n is 1, and Z is a 3-(dimethylamino)-1-propynyl group;
a compound of the formula (Ia), wherein n is 1, and Z is a 3-methoxy-1-propynyl group;
a compound of the formula (Ia), wherein n is 1, and Z is a 1-butynyl group;
a compound of the formula (Ia), wherein n is 1, and Z is a 4-(methoxycarbonyl)-1-butynyl group;
a compound of the formula (Ia), wherein n is 2, and Z is a 1-ethynyl group;
a compound of the formula (Ia), wherein n is 2, and Z is a 1-propynyl group;
a compound of the formula (Ia), wherein n is 2, and Z is a 3-fluoro-1-propynyl group;
a compound of the formula (Ia), wherein n is 2, and Z is a 2-propynyl group;
a compound of the formula (Ia), wherein n is 2, and Z is a 1-fluoro-2-propynyl group;
a compound of the formula (Ia), wherein n is 2, and Z is a 3-(dimethylamino)-1-propynyl group;
a compound of the formula (Ia), wherein n is 2, and Z is a 3-methoxy-1-propynyl group;
a compound of the formula (Ia), wherein n is 2, and Z is a 1-butynyl group;
a compound of the formula (Ia), wherein n is 2, and Z is a 4-(methoxycarbonyl)-1-butynyl group;
a compound of the formula (Ia), wherein n is 1, and Z is a 1-ethynyl group at the 3-position on the cyclopentane ring;
a compound of the formula (Ia), wherein n is 1, and Z is a 1-propynyl group at the 3-position on the cyclopentane ring;
a compound of the formula (Ia), wherein n is 1, and Z is a 3-fluoro-1-propynyl group at the 3-position on the cyclopentane ring;
a compound of the formula (Ia), wherein n is 1, and Z is a 2-propynyl group at the 3-position on the cyclopentane ring;
a compound of the formula (Ia), wherein n is 1, and Z is a 1-fluoro-2-propynyl group at the 3-position on the cyclopentane ring;
a compound of the formula (Ia), wherein n is 1, and Z is a 3-(dimethylamino)-1-propynyl group at the 3-position on the cyclopentane ring;
a compound of the formula (Ia), wherein n is 1, and Z is a 3-methoxy-1-propynyl group at the 3-position on the cyclopentane ring;
a compound of the formula (Ia), wherein n is 1, and Z is a 1-butynyl group at the 3-position on the cyclopentane ring;
a compound of the formula (Ia), wherein n is 1, and Z is a 4-(methoxycarbonyl)-1-butynyl group at the 3-position on the cyclopentane ring;
a compound of the formula (Ia), wherein n is 2, and Z is a 1-ethynyl group at the 3-position on the cyclopentane ring;
a compound of the formula (Ia), wherein n is 2, and Z is a 1-propynyl group at the 3-position on the cyclopentane ring;
a compound of the formula (Ia), wherein n is 2, and Z is a 3-fluoro-1-propynyl group at the 3-position on the cyclopentane ring;
a compound of the formula (Ia), wherein n is 2, and Z is a 2-propynyl group at the 3-position on the cyclopentane ring;
a compound of the formula (Ia), wherein n is 2, and Z is a 1-fluoro-2-propynyl group at the 3-position on the cyclopentane ring;
a compound of the formula (Ia), wherein n is 2, and Z is a 3-(dimethylamino)-1-propynyl group at the 3-position on the cyclopentane ring;
a compound of the formula (Ia), wherein n is 2, and Z is a 3-methoxy-1-propynyl group at the 3-position on the cyclopentane ring;
a compound of the formula (Ia), wherein n is 2, and Z is a 1-butynyl group at the 3-position on the cyclopentane ring; and
a compound of the formula (Ia), wherein n is 2, and Z is a 4-(methoxycarbonyl)-1-butynyl group at the 3-position on the cyclopentane ring.

The compound of the present invention also includes a compound of the formula (Ib):

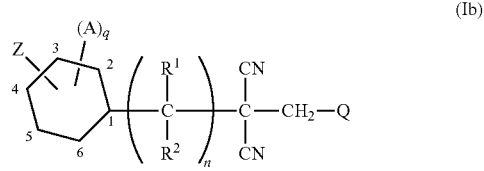

wherein A, n, q, Q, R$^1$, R$^2$ and Z are as defined above. Further, specific examples of the compound of the present invention include:

a compound of the formula (Ib), wherein Z is a 1-ethynyl group;
a compound of the formula (Ib), wherein Z is a 1-propynyl group;
a compound of the formula (Ib), wherein Z is a 3-fluoro-1-propynyl group;
a compound of the formula (Ib), wherein Z is a 2-propynyl group;
a compound of the formula (Ib), wherein Z is a 1-fluoro-2-propynyl group;
a compound of the formula (Ib), wherein Z is a 3-(dimethylamino)-1-propynyl group;
a compound of the formula (Ib), wherein Z is a 3-methoxy-1-propynyl group;
a compound of the formula (Ib), wherein Z is a 1-butynyl group;
a compound of the formula (Ib), wherein Z is a 4-(methoxycarbonyl)-1-butynyl group;
a compound of the formula (Ib), wherein n is 1, and Z is a 1-ethynyl group;
a compound of the formula (Ib), wherein n is 1, and Z is a 1-propynyl group;
a compound of the formula (Ib), wherein n is 1, and Z is a 3-fluoro-1-propynyl group;
a compound of the formula (Ib), wherein n is 1, and Z is a 2-propynyl group;
a compound of the formula (Ib), wherein n is 1, and Z is a 1-fluoro-2-propynyl group;
a compound of the formula (Ib), wherein n is 1, and Z is a 3-(dimethylamino)-1-propynyl group;
a compound of the formula (Ib), wherein n is 1, and Z is a 3-methoxy-1-propynyl group;
a compound of the formula (Ib), wherein n is 1, and Z is a 1-butynyl group;
a compound of the formula (Ib), wherein n is 1, and Z is a 4-(methoxycarbonyl)-1-butynyl group;
a compound of the formula (Ib), wherein n is 2, and Z is a 1-ethynyl group;
a compound of the formula (Ib), wherein n is 2, and Z is a 1-propynyl group;
a compound of the formula (Ib), wherein n is 2, and Z is a 3-fluoro-1-propynyl group;
a compound of the formula (Ib), wherein n is 2, and Z is a 2-propynyl group;
a compound of the formula (Ib), wherein n is 2, and Z is a 1-fluoro-2-propynyl group;
a compound of the formula (Ib), wherein n is 2, and Z is a 3-(dimethylamino)-1-propynyl group;
a compound of the formula (Ib), wherein n is 2, and Z is a 3-methoxy-1-propynyl group;
a compound of the formula (Ib), wherein n is 2, and Z is a 1-butynyl group;
a compound of the formula (Ib), wherein n is 2, and Z is a 4-(methoxycarbonyl)-1-butynyl group;
a compound of the formula (Ib), wherein n is 1, and Z is a 1-ethynyl group at the 3-position on the cyclohexane ring;
a compound of the formula (Ib), wherein n is 1, and Z is a 1-propynyl group at the 3-position on the cyclohexane ring;
a compound of the formula (Ib), wherein n is 1, and Z is a 3-fluoro-1-propynyl group at the 3-position on the cyclohexane ring;
a compound of the formula (Ib), wherein n is 1, and Z is a 2-propynyl group at the 3-position on the cyclohexane ring;
a compound of the formula (Ib), wherein n is 1, and Z is a 1-fluoro-2-propynyl group at the 3-position on the cyclohexane ring;
a compound of the formula (Ib), wherein n is 1, and Z is a 3-(dimethylamino)-1-propynyl group at the 3-position on the cyclohexane ring;
a compound of the formula (Ib), wherein n is 1, and Z is a 3-methoxy-1-propynyl group at the 3-position on the cyclohexane ring;
a compound of the formula (Ib), wherein n is 1, and Z is a 1-butynyl group at the 3-position on the cyclohexane ring;
a compound of the formula (Ib), wherein n is 1, and Z is a 4-(methoxycarbonyl)-1-butynyl group at the 3-position on the cyclohexane ring;
a compound of the formula (Ib), wherein n is 1, and Z is a 1-ethynyl group at the 4-position on the cyclohexane ring;
a compound of the formula (Ib), wherein n is 1, and Z is a 1-propynyl group at the 4-position on the cyclohexane ring;
a compound of the formula (Ib), wherein n is 1, and Z is a 3-fluoro-1-propynyl group at the 4-position on the cyclohexane ring;
a compound of the formula (Ib), wherein n is 1, and Z is a 2-propynyl group at the 4-position on the cyclohexane ring;
a compound of the formula (Ib), wherein n is 1, and Z is a 1-fluoro-2-propynyl group at the 4-position on the cyclohexane ring;
a compound of the formula (Ib), wherein n is 1, and Z is a 3-(dimethylamino)-1-propynyl group at the 4-position on the cyclohexane ring;
a compound of the formula (Ib), wherein n is 1, and Z is a 3-methoxy-1-propynyl group at the 4-position on the cyclohexane ring;
a compound of the formula (Ib), wherein n is 1, and Z is a 1-butynyl group at the 4-position on the cyclohexane ring;
a compound of the formula (Ib), wherein n is 1, and Z is a 4-(methoxycarbonyl)-1-butynyl group at the 4-position on the cyclohexane ring;
a compound of the formula (Ib), wherein n is 2, and Z is a 1-ethynyl group at the 3-position on the cyclohexane ring;
a compound of the formula (Ib), wherein n is 2, and Z is a 1-propynyl group at the 3-position on the cyclohexane ring;
a compound of the formula (Ib), wherein n is 2, and Z is a 3-fluoro-1-propynyl group at the 3-position on the cyclohexane ring;
a compound of the formula (Ib), wherein n is 2, and Z is a 2-propynyl group at the 3-position on the cyclohexane ring;
a compound of the formula (Ib), wherein n is 2, and Z is a 1-fluoro-2-propynyl group at the 3-position on the cyclohexane ring;
a compound of the formula (Ib), wherein n is 2, and Z is a 3-(dimethylamino)-1-propynyl group at the 3-position on the cyclohexane ring;
a compound of the formula (Ib), wherein n is 2, and Z is a 3-methoxy-1-propynyl group at the 3-position on the cyclohexane ring;
a compound of the formula (Ib), wherein n is 2, and Z is a 1-butynyl group at the 3-position on the cyclohexane ring;
a compound of the formula (Ib), wherein n is 2, and Z is a 4-(methoxycarbonyl)-1-butynyl group at the 3-position on the cyclohexane ring;
a compound of the formula (Ib), wherein n is 2, and Z is a 1-ethynyl group at the 4-position on the cyclohexane ring;
a compound of the formula (Ib), wherein n is 2, and Z is a 1-propynyl group at the 4-position on the cyclohexane ring;
a compound of the formula (Ib), wherein n is 2, and Z is a 3-fluoro-1-propynyl group at the 4-position on the cyclohexane ring;

a compound of the formula (Ib), wherein n is 2, and Z is a 2-propynyl group at the 4-position on the cyclohexane ring;
a compound of the formula (Ib), wherein n is 2, and Z is a 1-fluoro-2-propynyl group at the 4-position on the cyclohexane ring;
a compound of the formula (Ib), wherein n is 2, and Z is a 3-(dimethylamino)-1-propynyl group at the 4-position on the cyclohexane ring;
a compound of the formula (Ib), wherein n is 2, and Z is a 3-methoxy-1-propynyl group at the 4-position on the cyclohexane ring;
a compound of the formula (Ib), wherein n is 2, and Z is a 1-butynyl group at the 4-position on the cyclohexane ring;
a compound of the formula (Ib), wherein n is 2, and Z is a 4-(methoxycarbonyl)-1-butynyl group at the 4-position on the cyclohexane ring; and
a compound of the formula (Ib), wherein $R^1$ and $R^2$ are hydrogen atoms, n is 1 or 2, q is an integer of 0 to 2, Z is a C2-C4 alkynyl group or =N—$OR^3$, $R^3$ is a C1-C4 alkyl group or C2-C4 alkenyl group, and A is a halogen atom or hydroxyl group, or two A's form together —O—.

The compound of the present invention also includes a compound of the formula (Ic):

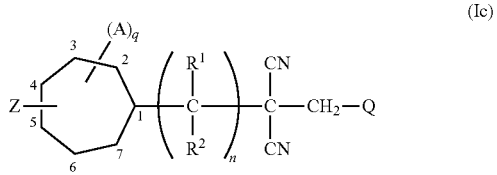

wherein A, n, q, Q, $R^1$, $R^2$ and Z are as defined above. Further, specific examples of the compound of the present invention include:
a compound of the formula (Ic), wherein Z is a 1-ethynyl group;
a compound of the formula (Ic), wherein Z is a 1-propynyl group;
a compound of the formula (Ic), wherein Z is a 3-fluoro-1-propynyl group;
a compound of the formula (Ic), wherein Z is a 2-propynyl group;
a compound of the formula (Ic), wherein Z is a 1-fluoro-2-propynyl group;
a compound of the formula (Ic), wherein Z is a 3-(dimethylamino)-1-propynyl group;
a compound of the formula (Ic), wherein Z is a 3-methoxy-1-propynyl group;
a compound of the formula (Ic), wherein Z is a 1-butynyl group;
a compound of the formula (Ic), wherein Z is a 4-(methoxycarbonyl)-1-butynyl group;
a compound of the formula (Ic), wherein n is 1, and Z is a 1-ethynyl group;
a compound of the formula (Ic), wherein n is 1, and Z is a 1-propynyl group;
a compound of the formula (Ic), wherein n is 1, and Z is a 3-fluoro-1-propynyl group;
a compound of the formula (Ic), wherein n is 1, and Z is a 2-propynyl group;
a compound of the formula (Ic), wherein n is 1, and Z is a 1-fluoro-2-propynyl group;
a compound of the formula (Ic), wherein n is 1, and Z is a 3-(dimethylamino)-1-propynyl group;
a compound of the formula (Ic), wherein n is 1, and Z is a 3-methoxy-1-propynyl group;
a compound of the formula (Ic), wherein n is 1, and Z is a 1-butynyl group;
a compound of the formula (Ic), wherein n is 1, and Z is a 4-(methoxycarbonyl)-1-butynyl group;
a compound of the formula (Ic), wherein n is 2, and Z is a 1-ethynyl group;
a compound of the formula (Ic), wherein n is 2, and Z is a 1-propynyl group;
a compound of the formula (Ic), wherein n is 2, and Z is a 3-fluoro-1-propynyl group;
a compound of the formula (Ic), wherein n is 2, and Z is a 2-propynyl group;
a compound of the formula (Ic), wherein n is 2, and Z is a 1-fluoro-2-propynyl group;
a compound of the formula (Ic), wherein n is 2, and Z is a 3-(dimethylamino)-1-propynyl group;
a compound of the formula (Ic), wherein n is 2, and Z is a 3-methoxy-1-propynyl group;
a compound of the formula (Ic), wherein n is 2, and Z is a 1-butynyl group;
a compound of the formula (Ic), wherein n is 2, and Z is a 4-(methoxycarbonyl)-1-butynyl group;
a compound of the formula (Ic), wherein n is 1, and Z is a 1-ethynyl group at the 3-position on the cycloheptane ring;
a compound of the formula (Ic), wherein n is 1, and Z is a 1-propynyl group at the 3-position on the cycloheptane ring;
a compound of the formula (Ic), wherein n is 1, and Z is a 3-fluoro-1-propynyl group at the 3-position on the cycloheptane ring;
a compound of the formula (Ic), wherein n is 1, and Z is a 2-propynyl group at the 3-position on the cycloheptane ring;
a compound of the formula (Ic), wherein n is 1, and Z is a 1-fluoro-2-propynyl group at the 3-position on the cycloheptane ring;
a compound of the formula (Ic), wherein n is 1, and Z is a 3-(dimethylamino)-1-propynyl group at the 3-position on the cycloheptane ring;
a compound of the formula (Ic), wherein n is 1, and Z is a 3-methoxy-1-propynyl group at the 3-position on the cycloheptane ring;
a compound of the formula (Ic), wherein n is 1, and Z is a 1-butynyl group at the 3-position on the cycloheptane ring;
a compound of the formula (Ic), wherein n is 1, and Z is a 4-(methoxycarbonyl)-1-butynyl group at the 3-position on the cycloheptane ring;
a compound of the formula (Ic), wherein n is 1, and Z is a 1-ethynyl group at the 4-position on the cycloheptane ring;
a compound of the formula (Ic), wherein n is 1, and Z is a 1-propynyl group at the 4-position on the cycloheptane ring;
a compound of the formula (Ic), wherein n is 1, and Z is a 3-fluoro-1-propynyl group at the 4-position on the cycloheptane ring;
a compound of the formula (Ic), wherein n is 1, and Z is a 2-propynyl group at the 4-position on the cycloheptane ring;
a compound of the formula (Ic), wherein n is 1, and Z is a 1-fluoro-2-propynyl group at the 4-position on the cycloheptane ring;
a compound of the formula (Ic), wherein n is 1, and Z is a 3-(dimethylamino)-1-propynyl group at the 4-position on the cycloheptane ring;
a compound of the formula (Ic), wherein n is 1, and Z is a 3-methoxy-1-propynyl group at the 4-position on the cycloheptane ring;
a compound of the formula (Ic), wherein n is 1, and Z is a 1-butynyl group at the 4-position on the cycloheptane ring;

a compound of the formula (Ic), wherein n is 1, and Z is a 4-(methoxycarbonyl)-1-butynyl group at the 4-position on the cycloheptane ring;
a compound of the formula (Ic), wherein n is 2, and Z is a 1-ethynyl group at the 3-position on the cycloheptane ring;
a compound of the formula (Ic), wherein n is 2, and Z is a 1-propynyl group at the 3-position on the cycloheptane ring;
a compound of the formula (Ic), wherein n is 2, and Z is a 3-fluoro-1-propynyl group at the 3-position on the cycloheptane ring;
a compound of the formula (Ic), wherein n is 2, and Z is a 2-propynyl group at the 3-position on the cycloheptane ring;
a compound of the formula (Ic), wherein n is 2, and Z is a 1-fluoro-2-propynyl at the 3-position on the cycloheptane ring;
a compound of the formula (Ic), wherein n is 2, and Z is a 3-(dimethylamino)-1-propynyl group at the 3-position on the cycloheptane ring;
a compound of the formula (Ic), wherein n is 2, and Z is a 3-methoxy-1-propynyl group at the 3-position on the cycloheptane ring;
a compound of the formula (Ic), wherein n is 2, and Z is a 1-butynyl group at the 3-position on the cycloheptane ring;
a compound of the formula (Ic), wherein n is 2, and Z is a 4-(methoxycarbonyl)-1-butynyl group at the 3-position on the cycloheptane ring;
a compound of the formula (Ic), wherein n is 2, and Z is a 1-ethynyl group at the 4-position on the cycloheptane ring;
a compound of the formula (Ic), wherein n is 2, and Z is a 1-propynyl group at the 4-position on the cycloheptane ring;
a compound of the formula (Ic), wherein n is 2, and Z is a 3-fluoro-1-propynyl group at the 4-position on the cycloheptane ring;
a compound of the formula (Ic), wherein n is 2, and Z is a 2-propynyl group at the 4-position on the cycloheptane ring;
a compound of the formula (Ic), wherein n is 2, and Z is a 1-fluoro-2-propynyl group at the 4-position on the cycloheptane ring;
a compound of the formula (Ic), wherein n is 2, and Z is a 3-(dimethylamino)-1-propynyl group at the 4-position on the cycloheptane ring;
a compound of the formula (Ic), wherein n is 2, and Z is a 3-methoxy-1-propynyl group at the 4-position on the cycloheptane ring;
a compound of the formula (Ic), wherein n is 2, and Z is a 1-butynyl group at the 4-position on the cycloheptane ring; and
a compound of the formula (Ic), wherein n is 2, and Z is a 4-(methoxycarbonyl)-1-butynyl group at the 4-position on the cycloheptane ring.

The compound of the present invention also includes a compound of the formula (Id):

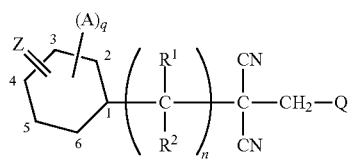

(Id)

wherein A, n, q, Q, $R^1$, $R^2$ and Z are as defined above. Further, specific examples of the compound of the present invention include:
a compound of the formula (Id), wherein Z is a methoxyimino group;
a compound of the formula (Id), wherein Z is a (1,1-dimethylethoxy)imino group;
a compound of the formula (Id), wherein Z is a (2-propenyloxy)imino group;
a compound of the formula (Id), wherein n is 1, and Z is a methoxyimino group;
a compound of the formula (Id), wherein n is 2, and Z is a methoxyimino group;
a compound of the formula (Id), wherein n is 1, and Z is a (1,1-dimethylethoxy)imino group;
a compound of the formula (Id), wherein n is 2, and Z is a (1,1-dimethylethoxy)imino group;
a compound of the formula (Id), wherein n is 1, and Z is a methoxyimino group at the 3-position on the cyclohexane ring;
a compound of the formula (Id), wherein n is 1, and Z is a methoxyimino group at the 4-position on the cyclohexane ring;
a compound of the formula (Id), wherein n is 2, and Z is a methoxyimino group at the 3-position on the cyclohexane ring;
a compound of the formula (Id), wherein n is 2, and Z is a methoxyimino group at the 4-position on the cyclohexane ring;
a compound of the formula (Id), wherein n is 1, and Z is a (1,1-dimethylethoxy)imino group at the 3-position on the cyclohexane ring;
a compound of the formula (Id), wherein n is 1, and Z is a (1,1-dimethylethoxy)imino group at the 4-position on the cyclohexane ring;
a compound of the formula (Id), wherein n is 2, and Z is a (1,1-dimethylethoxy)imino group at the 3-position on the cyclohexane ring; and
a compound of the formula (Id), wherein n is 2, and Z is a (1,1-dimethylethoxy)imino group at the 4-position on the cyclohexane ring.

Then, a process for producing the compound of the present compound is explained.

The compound of the present invention can be produced, for example, by the following Production Process 1 or Production Process 2.

Production Process 1

The compound of the present invention can be produced by reacting the following compound (a) and the following compound (b):

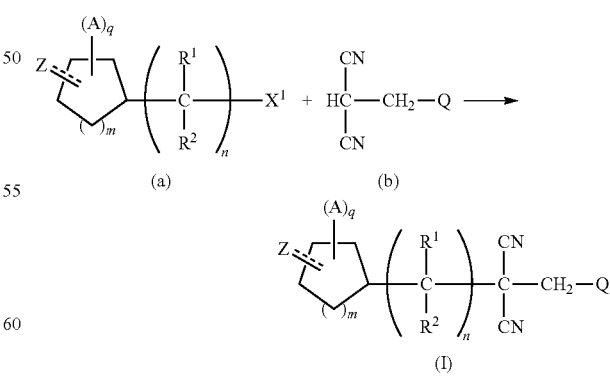

wherein, m, n, q, $R^1$, $R^2$, Q, Z and A are as defined above, and $X^1$ represents a chlorine atom, a bromine atom, an iodine atom, a methanesulfonyloxy group, a toluenesulfonyloxy group, or a trifluoromethanesulfonyloxy group.

The reaction is usually carried out in a solvent in the presence of a base.

Examples of the solvent include aliphatic hydrocarbons such as hexane, heptane, octane and cyclohexane, aromatic hydrocarbons such as toluene, xylene and mesitylene, ethers such as diethyl ether, methyl-tert-butyl ether, tetrahydrofuran and 1,4-dioxane, acid amides such as N,N-dimethylformamide, dialkyl sulfoxides such as dimethyl sulfoxide, and their mixtures.

Examples of the base include carbonates such as sodium carbonate and potassium carbonate, alkali metal hydrides such as sodium hydride, and tertiary amines such as triethylamine and diisopropylethylamine.

The amount of the compound (a) is usually from 1 to 10 mol per 1 mol of the compound (b).

The amount of the base used for the reaction is usually from 1 to 10 mol per 1 mol of the compound (b).

The reaction temperature is usually from −20 to 100° C., and the reaction time is usually from 0.1 to 24 hours.

After completion of the reaction, the compound of the present invention can be isolated by post-treatment, for example, by pouring a reaction mixture into water, extracting the mixture with an organic solvent, and drying and concentrating the resulting organic layer. The isolated compound of the present invention can be purified by chromatography, recrystallization or the like, if necessary.

Production Process 2

The compound of the present invention can be produced by reacting the following compound (c) with the following compound (d):

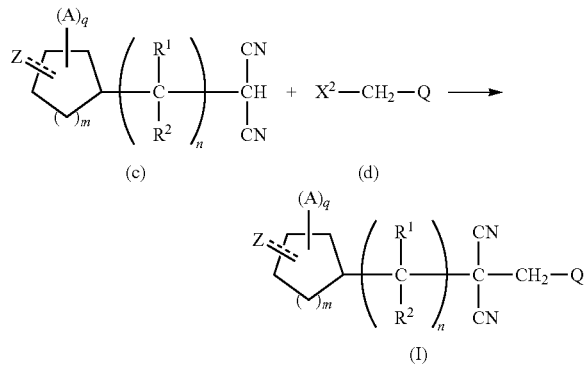

wherein, m, n, q, $R^1$, $R^2$, Q, Z and A are as defined above, and $X^2$ represents a chlorine atom, a bromine atom, an iodine atom, a methanesulfonyloxy group, a toluenesulfonyloxy group, or a trifluoromethanesulfonyloxy group.

The reaction is usually carried out in a solvent in the presence of a base.

Examples of the solvent include aliphatic hydrocarbons such as hexane, heptane, octane and cyclohexane, aromatic hydrocarbons such as toluene, xylene and mesitylene, ethers such as diethyl ether, methyl-tert-butyl ether, tetrahydrofuran and 1,4-dioxane, acid amides such as N,N-dimethylformamide, dialkyl sulfoxides such as dimethyl sulfoxide, and their mixtures.

Examples of the base include carbonates such as sodium carbonate and potassium carbonate, alkali metal hydrides such as sodium hydride, and tertiary amines such as triethylamine and diisopropylethylamine.

The amount of the compound (d) is usually from 1 to 10 mol per 1 mol of the compound (c).

The amount of the base used for the reaction is usually from 1 to 10 mol per 1 mol of the compound (c).

The reaction temperature is usually from −20 to 100° C., and the reaction time is usually from 0.1 to 24 hours.

After completion of the reaction, the compound of the present invention can be isolated by post-treatment, for example, by pouring a reaction mixture into water, extracting the mixture with an organic solvent, and drying and concentrating the resulting organic layer. The isolated compound of the present invention can be purified by chromatography, recrystallization or the like, if necessary.

Then, a process for producing an intermediate compound for production of the compound of the present invention is explained.

The compound (b) can be produced, for example, by reacting the compound (d) with malononitrile:

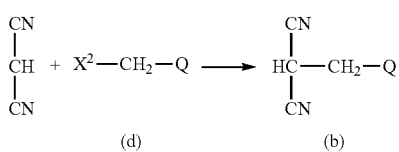

wherein Q and $X^2$ are as defined above.

The reaction is usually carried out in a solvent in the presence of a base.

Examples of the solvent include aliphatic hydrocarbons such as hexane, heptane, octane and cyclohexane, aromatic hydrocarbons such as toluene, xylene and mesitylene, ethers such as diethyl ether, methyl-tert-butyl ether, tetrahydrofuran and 1,4-dioxane, acid amides such as N,N-dimethylformamide, and their mixtures.

Examples of the base include carbonates such as sodium carbonate and potassium carbonate, alkali metal hydrides such as sodium hydride, and tertiary amines such as triethylamine and diisopropylethylamine.

The amount of malononitrile is usually from 1 to 10 mol per 1 mol of the compound (d).

The amount of the base used for the reaction is usually from 0.5 to 5 mol per 1 mol of the compound (d).

The reaction temperature is usually from −20 to 100° C., and the reaction time is usually from 0.1 to 24 hours.

After completion of the reaction, the compound (d) can be isolated by post-treatment, for example, by pouring a reaction mixture into water, extracting the mixture with an organic solvent, and drying and concentrating the resulting organic layer. The isolated compound (d) can be purified by chromatography, recrystallization or the like, if necessary.

The compound (c) can be produced, for example, by reacting the compound (a) with malononitrile:

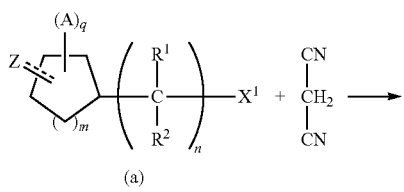

-continued

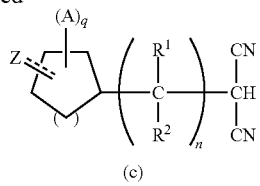

(c)

wherein, m, n, q, $R^1$, $R^2$, Z, A and $X^1$ are as defined above.

The reaction is usually carried out in a solvent in the presence of a base.

Examples of the solvent include aliphatic hydrocarbons such as hexane, heptane, octane and cyclohexane, aromatic hydrocarbons such as toluene, xylene and mesitylene, ethers such as diethyl ether, methyl-tert-butyl ether, tetrahydrofuran and 1,4-dioxane, acid amides such as N,N-dimethylformamide, and their mixtures.

Examples of the base include carbonates such as sodium carbonate and potassium carbonate, alkali metal hydrides such as sodium hydride, and tertiary amines such as triethylamine and diisopropylethylamine.

The amount of malononitrile is usually from 1 to 10 mol per 1 mol of the compound (a).

The amount of the base used for the reaction is usually from 0.5 to 5 mol per 1 mol of the compound (a).

The reaction temperature is usually from −20 to 100° C., and the reaction time is usually from 0.1 to 24 hours.

After completion of the reaction, the compound (c) can be isolated by post-treatment, for example, by pouring a reaction mixture into water, extracting the mixture with an organic solvent, and drying and concentrating the resulting organic layer. The isolated compound (c) can be purified by chromatography, recrystallization or the like, if necessary.

The compound (c) can be also produced by a method described in J. Chem. Soc. Perkin Trans. 1, 2589-2592 (1991).

The compound (a) can be produced in accordance with a known method.

Examples of arthropod pests on which the compound of the present invention exhibits a controlling effect include harmful insects and harmful mites, and more specifically, the following arthropods.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), citrus whitefly (*Dialeurodes citri*), and citrus spiny white fly (*Aleurocanthus spiniferus*); scales (Coccidae) such as Calformia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinus*), and white peach scale (*Pseudaulacaspis pentagona*); lace bugs (Tingidae); cimices such as Cimex lectularius; psyllids (Psyllidae), etc.;

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), *Ostrinia furnacalis*, cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana* fasciata), smaller tea tortrix (*Adoxophyes honmai*), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoniella*); Carposimidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*), etc.;

Thysanoptera:

Yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.;

Diptera:

Culices (Calicidae) such as common mosquito (*Culex pipiens pallens*), *Culex tritaeniorhynchus*, and Southern house mosquito (*Culex quinquefasciatus*); *Aedes* spp. such as yellow fever mosquito (*Aedes aegypti*), and Asian tiger mosquito (*Aedes albopictus*); *Anopheles* spp. such as *Anopheles sinensis*; Chironomidae; Houseflies (Muscidae) such as housefly (*Musca domestica*), and false stable fly (*Muscina stabulans*); blow flies (Calliphoridae); flesh flies (Sarcophagidae); little house flies (Fanniidae); anthomyiid flies (Anthomyiidae) such as seedcorn maggot (*Delia platura*), and onion maggot (*Delia antiqua*); leafminer flies (Agromyzidae) such as rice leafminer (*Agromyza oryzae*), rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloroidae) such as rice stem maggot (*Chlorops oryzae*); fruit flies (Tephritidae) such as melon fly (*Dacus cucurbitae*), and Mediteranean fruit fly (*Ceratitis capitata*); drosophila flies (Drosophilidae); humpbacked flies (Phoridae) such as *Megaselia spiracularis*; Psychodidae such as *Cloymia albipunctata*; Simuliidae; Tabanidae such as horsefly (*Tabanus trigonus*); stable flies (Stomoxys), etc.;

Coleoptera:

Corn root worms (*Diabrotica* spp.) such as Western corn root worm (*Diabrotica virgifera* virgifera), and Southern corn root worm (*Diabrotica undecimpunctata* howardi); scarabs (Scarabaeidae) such as cupreous chafer (*Anomala cuprea*), soybean beetle (*Anomala rufocuprea*), and Japanese beetle (*Popillia japonica*); weevils (Curculionidae) such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus venatus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); *Epilachna* such as twenty-eight-spotted ladybird (*Epilachna vigintioctopunctata*); bark beetles (Scolytidae) such as powder post beetle (*Lyctus brunneus*), and pine shoot beetle (*Tomicus piniperda*); false powderpost beetles (Bostrichidae); spider beetles (Ptinidae); longhorn beetles (Cerambycidae) such as white-spotted longicorn beetle (*Anoplophora malasiaca*); click beetles (*Agriotes* spp.); *Paederus fuscipes*, etc.;

Orthoptera:

Asiatic locust (*Locusta migratoria*), African mole cricket (*Gryllotalpa africana*), rice grasshopper (*Oxya yezoensis*), rice grasshopper (*Oxya japonica*), Grylloidea, etc.;

Siphonaptera:

Cat flea (*Ctenocephalides felis*), dog flea (*Ctenocephalides canis*), human flea (*Pulex irritans*), oriental rat flea (*Xenopsylla cheopis*), etc.;

Anoplura:

Human body louse (*Pediculus humanus corporis*), crab louse (*Phthirus pubis*), short-nosed cattle louse (*Haematopinus eurysternus*), sheep louse (*Damalinia ovis*), hog louse (*Haematopinus suis*), etc.;

Hymenoptera:

Ants (Formicidae) such as *Monomorium pharaonis*, *Formica fusca japonica*, black house ant (*Ochetellus glaber*), *Pristomyrmex pungens*, *Pheidole noda*, leaf-cutting ant (*Acromyrmex* spp.), and fire ant (*Solenopsis* spp.); hornets (Vespidae); bethylid wasps (Betylidae); sawflies (Tenthredimidae) such as Cabbage sawfly (*Athalia rosae*), and *Athalia japonica*, etc.;

Blattodea:

Cockroaches (Blattariae) such as German cockroach (*Blattella germanica*), smokybrown cockroach (*Periplaneta fuliginosa*), American cockroach (*Periplaneta americana*), *Periplaneta* brunnea, and oriental cockroach (*Blatta orientalis*);

Isoptera:

Termites (Termitidae) such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, Japanese dampwood termite (*Hodotermopsis japonica*), *Coptotermes guangzhoensis*, *Reticulitermes miyatakei*, *Reticulitermes flavipes amamianus*, *Reticulitermes* sp., *Nasutitermes takasagoensis*, *Pericapritermes nitobei*, *Sinocapritermes mushae*, etc.;

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis*, *Haemaphysalis flava*, *Dermacentor taiwanicus*, American dog tick (*Dermacentor variabilis*), *Ixodes ovatus*, *Ixodes persulcatus*, black legged tick (*Ixodes scapularis*), lone star tick (*Amblyomma americanum*), *Boophilus microplus*, and *Rhipicephalus sanguineus*; Psoroptidae such as ear mite (*Otodectes cynotis*); itch mites (Sarcoptidae) such as *Sarcoptes scabiei*; folicle mites (Demodicidae) such as dog folicle mite (*Demodex canis*); acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus*, *Cheyletus malaccensis*, and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*), etc.;

Chilopoda: *Thereuonema hilgendorfi*, *Scolopendra subspinipes*, etc.;

Diplopoda: garden millipede (*Oxidus gracilis*), *Nedyopus tambanus*, etc.;

Isopoda: common pill bug (*Armadillidium vulgare*), etc.;

Gastropoda: *Limax marginatus*, *Limax flavus*, etc.

Although the pesticidal composition of the present invention may be the compound of the present invention itself, the pesticidal composition of the present invention usually comprises the compound of the present invention in combination with a solid carrier, a liquid carrier and/or a gaseous carrier, and if necessary, a surfactant or other pharmaceutical additives and takes the form of an emulsifiable concentrate, an oil solution, a shampoo formulation, a flowable formulation, a dust, a wettable powder, a granule, a paste formulation, a microcapsule formulation, a foam formulation, an aerosol formulation, a carbon dioxide gas formulation, a tablet, a resin formulation or the like. The pesticidal composition of the present invention may be processed into a poison bait, a mosquito coil, an electric mosquito mat, a smoking pesticide, a fumigant or a sheet, and then be used.

The pesticidal composition of the present invention usually contains 0.1 to 95% by weight of the compound of the present invention.

Examples of the solid carrier include finely-divided powder and granules of clay (e.g., kaolin clay, diatomaceous earth, bentonite, Fubasami clay, or acid clay), synthetic hydrated silicon oxide, talc, ceramics, other inorganic minerals (e.g., sericite, quartz, sulfur, activated carbon, calcium carbonate, or hydrated silica), and chemical fertilizers (e.g., ammonium sulfate, ammonium phosphate, ammonium nitrate, ammonium chloride, or urea).

Examples of the liquid carrier include aromatic or aliphatic hydrocarbons (e.g., xylene, toluene, alkylnaphthalene, phenylxylylethane, kerosene, light oil, hexane, or cyclohexane), halogenated hydrocarbons (e.g., chlorobenzene, dichloromethane, dichloroethane, or trichloroethane), alcohols (e.g., methanol, ethanol, isopropyl alcohol, butanol, hexanol, or ethylene glycol), ethers (e.g., diethylether, ethylene glycol dimethyl ether, diethylene glycol monomethyl ether, diethylene glycol monoethyl ether, propylene glycol monomethyl ether, tetrahydrofuran, or dioxane), esters (e.g., ethyl acetate, or butyl acetate), ketones (e.g., acetone, methyl ethyl ketone, methyl isobutyl ketone, or cyclohexanone), nitriles (e.g., acetonitrile, or isobutyronitrile), sulfoxides (e.g., dimethyl sulfoxide), acid amides (e.g., N,N-dimethylformamide, or N,N-dimethylacetamide), vegetable oils (e.g., soybean oil, or cottonseed oil), and vegetable essential oils (e.g., orange oil, hyssop oil, or lemon oil), water.

Examples of the gaseous carrier include butane gas, chlorofluorocarbon, liquefied petroleum gas (LPG), dimethyl ether, and carbon dioxide gas.

Examples of the surfactant include alkyl sulfate salts, alkyl sulfonate salts, alkylaryl sulfonate salts, alkyl aryl ethers and their polyoxyethylated derivatives, polyethylene glycol ethers, polyhydric alcohol esters, and sugar alcohol derivatives.

Examples of other formulation additives include a binder, a dispersant, and a stabilizer. Specific examples thereof include casein, gelatin, polysaccharides (e.g., starch, gum arabic, cellulose derivatives, or alginic acid), lignin derivatives, bentonite, saccharides, synthetic water-soluble polymers (e.g., polyvinyl alcohol, polyvinylpyrrolidone, or polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids, and fatty acid esters.

Examples of a base material for a resin formulation include vinyl chloride polymers, and polyurethane. To the base material, if necessary, a plasticizer such as phthalate (e.g., dimethyl phthalate, or dioctyl phthalate), adipate, stearic acid or the like may be added. The resin formulation is obtained by kneading the compound of the present invention into the base material using a conventional kneading apparatus, followed by molding such as injection molding, extrusion molding, press molding or the like. The resulting resin formulation may be formed into the shape of a plate, a film, a tape, a net, a string or the like via a further step of molding, cutting, or the like, if necessary. These resin formulations may be used, for example, in the form of an animal collar, an animal ear tag, a sheet formulation, a lead, or a horticultural post.

Examples of a base material of a poison bait include cereal powder, vegetable oil, sugar, and crystalline cellulose. To the base material, if necessary, an antioxidant such as dibutylhydroxytoluene or nordihydroguaiaretic acid, a preservative such as dehydroacetic acid, an agent for preventing children or pets from eating the poison bait by mistake such as hot pepper powder, a pest-attractive perfume such as cheese perfume, onion perfume or peanut oil or the like may be added.

The pesticidal composition of the present invention can be applied, for example, to arthropod pests directly and/or habitats of arthropod pests (e.g., plant bodies, animal bodies, or soil).

When the pesticidal composition of the present invention is used for controlling pests in agriculture and forestry, the application amount is usually 1 to 10,000 g/ha, preferably 10 to 500 g/ha of the compound of the present invention. When the pesticidal composition of the present invention is in the form of an emulsifiable concentrate, a wettable powder, a flowable formulation or a microcapsule formulation, it is usually used after dilution with water so as to contain 1 to 1,000 ppm of the compound of the present invention. When the pesticidal composition of the present invention is in the form of a dust or a granule, it is usually used as it is. The pesticidal composition of the present invention may be sprayed directly to plants to be protected from arthropod pests. Soil can be treated with the pesticidal composition of the present invention to control arthropod pests living in the soil. Seedbeds before planting or planting holes or plant feet in planting can be also treated with the pesticidal composition of the present invention. A sheet formulation of the pesticidal composition of the present invention may be applied by winding around plants, disposing in the vicinity of plants, laying on the soil surface at the plant feet, or the like.

The pesticidal composition of the present invention can be used in crop lands such as cultivated lands, paddy fields, lawns and orchards. The pesticidal composition of the present invention may control harmful arthropods in a crop land without causing drug damage to crop plants cultivated in the crop land.

Examples of such crop plants include

Agricultural crops: corn, rice, wheat, barley, rye, oat, sorghum, cotton, soybean, peanut, sarrazin, sugar beet, rapeseed, sunflower, sugar cane, tobacco etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid etc.;

Flowers;

Foliage plant;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, *macadamia* nut etc.), berry fruits (blueberry, cranberry, blackberry, raspberry etc.), grape, persimmon, olive, loquat, banana, coffee, date, coconut etc.;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) etc.

The aforementioned crop plants include crop plants having resistance to herbicides, for example, an HPPD inhibitor such as isoxaflutole, an ALS inhibitor such as imazethapyr or thifensulfuron-methyl, an EPSP synthesizing enzyme inhibitor, a glutamine synthesizing enzyme inhibitor, an acetyl CoA carboxylase inhibitor, or bromoxynil, which resistance is imparted by a classical breeding method, a genetic engineering technique or the like.

Examples of the crop plant having herbicide resistance imparted by a classical breeding method include Clearfield™ canola resistant to an imidazolinone herbicide such as imazethapyr, and STS soybean resistant to a sulfonylurea ALS inhibitor herbicide such as thifensulfuron-methyl, Examples of the crop plant having resistance to an acetyl CoA carboxylase inhibitor such as a trione oxime herbicide or an aryloxy phenoxypropionic acid herbicide include SR corn. The crop plants having resistance to acetyl CoA carboxylase inhibitors are found in, for example, Proc. Natl. Acad. Sci. USA 1990, 87, p. 7175-7179. In addition, a mutant acetyl CoA carboxylase resistant to an acetyl CoA carboxylase inhibitor is known, for example, in Weed Science 53: p. 728-746, 2005. When a gene encoding the mutant acetyl CoA carboxylase is introduced into a crop plant by a genetic engineering technique or when a mutation related to impartation of resistance is introduced into a gene encoding acetyl CoA carboxylase of a crop plant, a crop plant having the resistance to an acetyl CoA carboxylase inhibitor can be produced. Nucleic acids for introduction of a base substitution mutation can be introduced into the cell of a crop plant by chimeraplasty (see, Gura T. 1999, Repairing the Genome's Spelling Mistakes, Science 285: 316-318) to induce a site-directed amino acid mutation in the gene targeting an acetyl CoA carboxylase inhibitor or herbicide of the crop plant, and thereby a crop plant resistant to an acetyl CoA carboxylase inhibitor or herbicide can be produced.

Examples of the crop plant having herbicide resistance imparted by a genetic engineering technique include corn cultivars having resistance to glyphosate or glufosinate. Some of such corn cultivars are sold under the trade name of RoundupReady™, LibertyLink™, and the like.

The aforementioned crop plants include craop plants having an ability to produce an insecticidal toxin, for example a selective toxin originated from *Bacillus*, which ability is imparted by a genetic engineering technique.

Examples of the insecticidal toxin which is produced by such a genetically engineered plant include insecticidal proteins derived from *Bacillus cereus* and *Bacillus popilliae*; δ-endotoxins derived from *Bacillus thuringiensis*, such as Cry1Ab, Cry1Ac, Cry1F, Cry1Fa2, Cry2Ab, Cry3A, Cry3Bb1 and Cry9C; insecticidal proteins derived from *Bacillus thuringiensis*, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl syntase; chitinase; and glucanase.

The insecticidal toxin produced by such a genetically engineered plant also includes hybrid toxins of different insecticidal proteins, for example, selected from δ-endotoxins such as Cry1Ab, Cry1Ac, Cry1F, Cry1Fa2, Cry2Ab, Cry3A, Cry3Bb1 and Cry9C and insecticidal proteins such as VIP 1, VIP 2, VIP 3 and VIP 3A, and toxins in which a part of amino acids constituting an insecticidal protein is deleted or modified. The hybrid toxin is made by combining different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a naturally occurring toxin are substituted.

The insecticidal toxin and the genetically engineered crop plant having the ability to produce the insecticidal toxin are described, for example, in EP-A-C374 753, WO 93/07278, WO 95/34656, EP-A-C427 529, EP-A-451878, WO 03/052073, and the like.

The genetically engineered crop plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard™ (a corn cultivar expressing Cry1Ab toxin), YieldGard Rootworm™ (a corn cultivar expressing Cry3Bb1 toxin), YieldGard Plus™ (a corn cultivar expressing Cry1Ab and Cry3Bb1 toxins), Heculex I™ (a corn cultivar expressing Cry1Fa2 toxin and phosphinothricin N-acetyltransferase (PAT) for imparting resistance to glufosinate), NuCOTN33B™ (a cotton cultivar expressing Cry1Ac toxin), Bollgard I™ (a cotton cultivar expressing Cry1Ac toxin), Bollgard II™ (a cotton cultivar expressing Cry1Ac and Cry2Ab toxins), VIPCOT™ (a cotton cultivar expressing VIP toxin), NewLeaf™ (a potato cultivar expressing Cry3A toxin), NatureGard Agrisure GT Advantage™ (GA21 glyphosate-resistance character), Agrisure CB Advantage™ (Bt11 corn borer (CB) character), and Protecta™.

The aforementioned crop plants include those having an ability to produce an anti-pathogen substance which ability is imparted by a genetic engineering technique.

Examples of the anti-pathogen substance include PR proteins (PRPs, described in EP-A-C392 225); ion channel inhibitors such as sodium channel inhibitors, and calcium channel inhibitors (e.g. KP1, KP4, or KP6 toxins produced by viruses); stilbene synthase; bibenzyl synthase; chitinase; glucanase; and substances produced by microorganisms such as peptide antibiotics, heterocycle-containing antibiotics, and protein factors involved in plant disease-resistance (described in WO 03/000906). Such anti-pathogen substances and genetically engineered plants which produce the anti-pathogen substances are described in EP-A-C392 225, WO 05/33818, EP-A-C353 191, and the like.

When the pesticidal composition of the present invention is used for control of epidemic, the application amount is usually 0.001 to 10 mg/m$^3$ of the compound of the present invention for application to space, and 0.001 to 100 mg/m$^2$ of the compound of the present invention for application to a plane. The pesticidal composition in the form of an emulsifiable concentrate, a wettable powder or a flowable formulation is usually applied after dilution with water so as to contain usually 0.001 to 10,000 ppm of the compound of the present invention. The pesticidal composition in the form of an oil solution, an aerosol formulation, a smoking pesticide or a poison bait is usually applied as it is.

When the pesticidal composition of the present invention is used for controlling external parasites of livestock such as a cow, a horse, a pig, a sheep, a goat and a chicken, or small animals such as a dog, a cat, a rat and a mouse, it can be applied to said animals by a known method in the veterinary field. Specifically, when systemic control is intended, the pesticidal composition of the present invention is administered, for example, as a tablet, a mixture with feed, a suppository or an injection (e.g., intramuscularly, subcutaneously, intravenously, or intraperitoneally). When non-systemic control is intended, the pesticidal composition of the present invention is applied to an animal by spraying, pour-on treatment or a spot-on treatment with the pesticidal composition in the form of an oil solution or an aqueous liquid, washing the animal with the pesticidal composition in the form of a shampoo formulation, and attaching a collar or a ear tag made of the pesticidal composition in the form of a resin formulation to the animal. When administered to an animal, the amount of the compound of the present invention is usually in the range of 0.1 to 1,000 mg per 1 kg body weight of the animal.

The pesticidal composition of the present invention may be used in admixture or combination with other insecticides, nematocides, acaricides, fungicides, herbicides, plant growth regulators, synergists, fertilizers, soil conditioners, animal feed, and the like.

Examples of an active ingredient of such insecticide include:

(1) organic phosphorus compounds:

acephate, aluminium phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), didhlofenthion (ECP), didhlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like;

(2) carbamate compounds:

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, and the like;

(3) synthetic pyrethroid compounds:

acrinathrin, allethrin, beta-cyfluthrin, bifenthrin, cyclopro-thrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, and the like;

(4) nereistoxin compounds:

cartap, bensultap, thiocyclam, monosultap, bisultap, and the like;

(5) neonicotinoid compounds:

imidacloprid, nitenpyram, acetamiprid, thiamethoxam, thiacloprid, dinotefuran, clothianidin, and the like;

(6) benzoylurea compounds:

chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) phenylpyrazole compounds:

acetoprole, ethiprole, fipronil, vaniliprole, pyriprole, pyrafluprole, and the like;

(8) Bt toxin insecticides:

live spores or crystal toxins originated from *Bacillus* thuringiesis and a mixture thereof;

(9) hydrazine compounds:

chromafenozide, halofenozide, methoxyfenozide, tebufenozide, and the like;

(10) organic chlorine compounds:

aldrin, dieldrin, dienochlor, endosulfan, methoxychlor, and the 111e;

(11) natural insecticides:

machine oil, nicotine-sulfate;

(12) other insecticides:

avermectin-B, bromopropylate, buprofezin, chlorphenapyr, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, spinetoram, chlorantraniliprole, tralopyril, a compound represented by the formula (A):

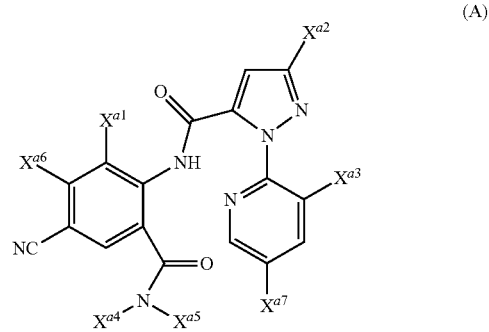

(A)

wherein $X^{a1}$ represents a methyl group, a chlorine atom, a bromine atom or a fluorine atom, $X^{a2}$ represents a fluorine atom, a chlorine atom, a bromine atom, a C1-C4 haloalkyl group or a C1-C4 haloalkoxy group, $X^{a3}$ represents a fluorine atom, a chlorine atom or a bromine atom, $X^{a4}$ represents an optionally substituted C1-C4 alkyl group, an optionally substituted C3-C4 alkenyl group, an optionally substituted C3-C4 alkynyl group, an optionally substituted C3-C5 cycloalkylalkyl group or a hydrogen atom, $X^{a5}$ represents a hydrogen atom, a fluorine atom or a chlorine atom, $X^{a6}$ represents a hydrogen atom, a fluorine atom or a chlorine atom, and $X^{a7}$ represents a hydrogen atom, a fluorine atom or a chlorine atom; a compound represented by the formula (B):

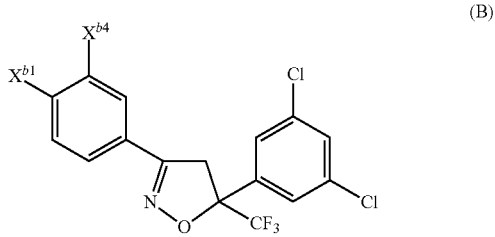

(B)

wherein $X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group or an optionally substituted 1,2,4-triazol-1-yl group, $X^{b2}$ represents an optionally substituted C1-C4 haloalkyl group such as a 2,2,2-trifluoroethyl group, or an optionally substituted C3-C6 cycloalkyl group such as a cyclopropyl group, $X^{b3}$ represents an optionally substituted C1-C4 alkyl group such as methyl, and $X^{b4}$ represents a hydrogen atom, chlorine atom, a cyano group or a methyl group; and a compound represented by the formula (C):

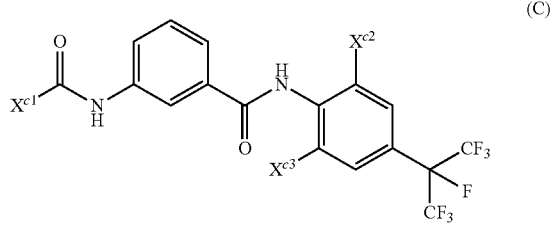

(C)

wherein $X^{c1}$ represents an optionally substituted C1-C4 alkyl group such as a 3,3,3-trifluoropropyl group, an optionally substituted C1-C4 alkoxy group such as a 2,2,2-trichloroethoxy group, an optionally substituted phenyl group such as a 4-cyanophenyl group, or an optionally substituted pyridyl group such as a 2-chloro-3-pyridyl group, $X^{c2}$ represents a methyl group or a trifluoromethyl group, and $X^{c3}$ represents a methyl group or a halogen atom.

Examples of an active ingredient of the acaricide include acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet, and cyenopyrafen.

Example of an active ingredient of the nematocide include DCIP, fosthiazate, levamisol, methylisothiocyanate, morantel tartarate, and imicyafos.

Examples of an active ingredient of the fungicide include strobilurin compounds such as azoxystrobin; organophosphate compounds such as tolclofos-methyl; azole compounds such as triflumizole, pefurazoate and difenoconazole; fthalide, flutolanil, validamycin, probenazole, diclomezine, pencycuron, dazomet, kasugamycin, pyroquilon, oxolinic acid, tricyclazole, ferimzone, mepronil, EDDP, isoprothiolane, carpropamid, diclocymet, furametpyr, fludioxonil, procymidone and diethofencarb.

EXAMPLES

Hereinafter, the present invention is described in more detail by way of Production Examples, Formulation Examples and Test Examples. However, the present invention is not limited to these Examples.

First, Production Examples of the compound of the present invention are shown.

Production Example 1

Step 1-1

A solution of 19.04 g of oxalyl chloride in 200 mL of dichloromethane was cooled to −78° C. under a nitrogen atmosphere. To the solution was added dropwise a solution of 11.72 g of dimethyl sulfoxide in 50 mL of dichloromethane over 20 minutes, followed by stirring at −50° C. for 30 minutes. To the reaction mixture was added dropwise a solution of 22.83 g of 4-[[(tetrahydro-2H-pyran-2-yl)oxy]methyl]cyclohexanemethanol (trans/cis=6/4) in 50 mL of dichloromethane over 30 minutes, followed by stirring at −50° C. for 40 minutes. To the mixture was added dropwise 30.36 g of triethylamine over 40 minutes. The reaction mixture was stirred at room temperature for 18 hours. To the reaction mixture was added 100 mL of water. An organic layer was separated and then extracted twice with 100 mL of chloroform. The combined organic layer was washed sequentially with 150 mL of a 1 N aqueous hydrochloric acid solution, 150 mL of a saturated aqueous sodium hydrogen carbonate solution and then 150 mL of water, dried over sodium sulfate, filtered and then concentrated under reduced pressure. The residue was subjected to silica gel column chromatography to give 20.04 g of 4-[[(tetrahydro-2H-pyran-2-yl)oxy]methyl]cyclohexanecarbaldehyde represented by the following formula:

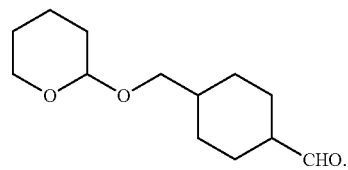 [SMILES: O=CC1CCC(COC2CCCCO2)CC1]

The compound was a mixture of a trans-isomer and a cis-isomer in the trans/cis ratio of about 3/1.

Step 1-2

To a solution of 39.80 g of carbon tetrabromide in 180 mL of dichloromethane was added 62.95 g of triphenylphosphine under a nitrogen atmosphere over 1 hour. The mixture was stirred for 30 minutes. To the solution was added dropwise a solution of 13.35 g of 4-[[(tetrahydro-2H-pyran-2-yl)oxy] methyl]cyclohexanecarbaldehyde (trans/cis=about 3/1) in 120 mL of dichloromethane over 30 minutes, followed by stirring at room temperature for 22 hours. To the reaction mixture was added 150 mL of t-butylmethyl ether, and insoluble substances were filtered. Then, the filtrate was concentrated under reduced pressure. The residue was subjected to silica gel column chromatography to give 12.89 g of 1-bromomethyl-4-(2,2-dibromovinyl)cyclohexane represented by the following formula:

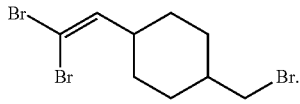 [SMILES: BrCC1CCC(C=C(Br)Br)CC1]

The compound was a mixture of a trans-isomer and a cis-isomer in the trans/cis ratio of about 3/1.

Trans-1-bromomethyl-4-(2,2-dibromovinyl)cyclohexane

¹H-NMR (CDCl₃, TMS, δ (ppm)): 1.07-1.26 (4H, m), 1.56-1.59 (1H, m), 1.82-1.94 (4H, m), 2.15-2.33 (1H, m), 3.28 (2H, d), 6.19 (1H, d).

Cis-1-bromomethyl-4-(2,2-dibromovinyl)cyclohexane

¹H-NMR (CDCl₃, TMS, δ(ppm)): 1.07-2.05 (9H, m), 2.51-2.60 (1H, m), 3.35 (2H, d), 6.50 (1H, d).

Step 1-3

A solution of 8.36 g of 1-bromomethyl-4-(2,2-dibromovinyl)cyclohexane (trans/cis=about 3/1) in 20 mL of tetrahydrofuran was cooled to −78° C. under a nitrogen atmosphere. To the solution was added dropwise 24.3 mL of a 2.1 M methyl lithium diethyl ether solution over 30 minutes, followed by stirring for 2 hours while maintaining a temperature of −78° C. The reaction mixture was cooled in an ice bath, and 30 mL of a 1 N aqueous hydrochloric acid solution was added thereto. The reaction mixture was extracted with 30 mL of t-butyl methyl ether three times. The combined organic layer was washed sequentially with 100 mL of a saturated aqueous sodium hydrogen carbonate solution and 100 mL of a saturated aqueous sodium chloride solution, dried over sodium sulfate, filtered, and then concentrated under reduced pressure. The residue was subjected to silica gel column chromatography to give 4.68 g of 1-bromomethyl-4-ethynylcyclohexane represented by the following formula:

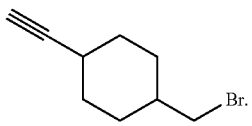

The compound was a mixture of a trans-isomer and a cis-isomer in the trans/cis ratio of about 3/1.

Trans-1-bromomethyl-4-ethynylcyclohexane

¹H-NMR (CDCl₃, TMS, δ (ppm)): 0.97-1.06 (2H, m), 1.35-1.46 (2H, m), 1.57-2.27 (7H, m), 3.27 (2H, d).

Cis-1-bromomethyl-4-ethynylcyclohexane

¹H-NMR (CDCl₃, TMS, δ (ppm)): 1.39-2.06 (10H, m), 2.73-2.79 (1H, m) 3.30 (2H, d).

Step 1-4

To a solution of 3.68 g of 1-bromomethyl-4-ethynylcyclohexane (trans/cis=about 3/1) in 20 mL of N,N-dimethylformamide were added 3.13 g of 3,3,3-trifluoropropylmalononitrile, 3.21 g of potassium iodide and 2.67 g of potassium carbonate, followed by stirring at 70° C. for 5 hours. The reaction mixture was cooled to room temperature and then 50 mL of a 1 N aqueous hydrochloric acid solution was added thereto. The reaction mixture was extracted three times with 30 mL of ethyl acetate. The combined organic layer was washed sequentially with 100 mL of a saturated aqueous sodium hydrogen carbonate solution and 100 mL of a saturated aqueous sodium chloride solution, dried over sodium sulfate, filtered, and then concentrated under reduced pressure. The residue was subjected to silica gel column chromatography to give 3.20 g of the trans isomer (hereinafter referred to as the present compound (1t)) and 1.01 g of the cis isomer (hereinafter referred to as the present compound (1c)) of 1-(2,2-dicyano-5,5,5-trifluoropentyl)-4-ethynylcyclohexane (hereinafter referred to as the present compound (1)) represented by the following formula:

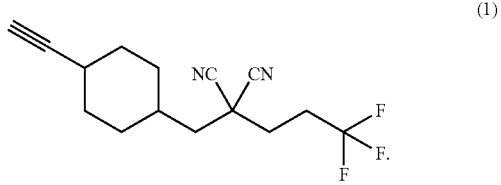 [SMILES: C#CC1CCC(CC(C#N)(C#N)CCC(F)(F)F)CC1]

Trans-1-(2,2-dicyano-5,5,5-trifluoropentyl)-4-ethynylcyclohexane (1t)

¹H-NMR (CDCl₃, TMS, δ (ppm)): 1.07-1.17 (2H, m), 1.43-1.53 (2H, m), 1.73-1.83 (1H, m), 1.87 (2H, d), 1.98-2.08 (5H, m), 2.17-2.26 (3H, m), 2.46-2.58 (2H, m). Cis-1-(2,2-dicyano-5,5,5-trifluoropentyl)-4-ethynylcyclohexane (1c)

¹H-NMR (CDCl₃, TMS, δ(ppm)): 1.55-1.65 (4H, m), 1.76-1.86 (5H, m), 1.92 (2H, d), 2.07 (1H, d), 2.17-2.23 (2H, m), 2.47-2.58 (2H, m), 2.80 (1H, m).

Production Example 2

Step 2-1

To a solution of 12.06 g or 1,4-dioxaspiro[4.5]decane-8-methanol in 70 mL of pyridine was added 15.20 g of p-toluenesulfonyl chloride, followed by stirring at room temperature for 5 hours. To the reaction mixture was added 200 mL of a 1 N aqueous hydrochloric acid solution, followed by extraction twice with 100 mL of ethyl acetate. The combined organic layer was washed sequentially with 100 mL of a 1 N aqueous hydrochloric acid solution twice, 100 mL of a saturated aqueous sodium hydrogen carbonate solution once, and 100 mL of a saturated aqueous sodium chloride solution once, dried over sodium sulfate, filtered, and then concentrated under reduced pressure. The residue was subjected to silica gel column chromatography to give 22.10 g of 1,4-dioxaspiro

[4.5]deca-8-ylmethyl p-toluenesuofonate represented by the following formula:

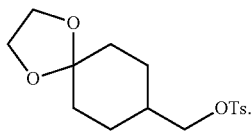 [SMILES: Cc1ccc(S(=O)(=O)OCC2CCC3(CC2)OCCO3)cc1]

$^1$H-NMR (CDCl$_3$, TMS, δ (ppm)): 1.17-1.28 (2H, m), 1.43-1.57 (3H, m), 1.71-1.73 (4H, m), 2.45 (3H, S), 3.83 (2H, d), 3.88-3.95 (4H, m), 7.33 (2H, d), 7.77 (2H, d).

Step 2-2

To a solution of 22.10 g of 1,4-dioxaspiro[4.5]deca-ylmethyl p-toluenesulfonate in 70 mL of N,N-dimethylformamide were added 12.16 g of 3,3,3-trifluoropropylmalononitrile, 12.45 g of potassium iodide and 10.37 g of potassium carbonate, followed by stirring at 70° C. for 5 hours. The reaction mixture was cooled to room temperature and then 200 mL of a 1 N aqueous hydrochloric acid solution was added thereto. The mixture was extracted twice with 200 mL of ethyl acetate. The combined organic layers was washed sequentially with 200 mL of a saturated aqueous sodium hydrogen carbonate solution and 200 mL of a saturated aqueous sodium chloride solution, dried over sodium sulfate, filtered, and then concentrated under reduced pressure. The residue was subjected to silica gel column chromatography to give 18.63 g of 8-(2,2-dicyano-5,5,5-trifluoropenyl)-1,4-dioxaspiro[4.5]decane represented by the following formula:

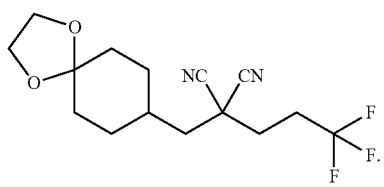 [SMILES: N#CC(C#N)(CCC(F)(F)F)CC1CCC2(CC1)OCCO2]

$^1$H-NMR (CDCl$_3$, TMS, δ(ppm)): 1.41-1.52 (2H, m), 1.56-1.65 (2H, m), 1.77-1.87 (3H, m), 1.91-1.97 (4H, m), 2.17-2.23 (2H, m), 2.47-2.58 (2H, m), 3.91-3.99 (4H, m).

Step 2-3

To 10 mL of a 50% aqueous acetic acid solution was added 3.16 g of 8-(2,2-dicyano-5,5,5-trifluorophenyl)-1,4-dioxaspiro[4.5]decane, followed by stirring at 50° C. under a nitrogen atmosphere for 8 hours. To the reaction mixture was added 100 mL of water, followed by extraction twice with 100 mL of ethyl acetate. The combined organic layer was washed sequentially with 100 mL of a saturated aqueous sodium hydrogen carbonate solution and 100 mL of a saturated aqueous sodium chloride solution, dried over sodium sulfate, filtered, and then concentrated under reduced pressure. The residue was subjected to silica gel column chromatography to give 2.28 g of 4-(2,2-dicyano-5,5,5-trifluoropentyl)cyclohexanone represented by the following formula:

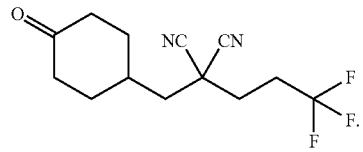 [SMILES: N#CC(C#N)(CCC(F)(F)F)CC1CCC(=O)CC1]

$^1$H-NMR (CDCl$_3$, TMS, δ(ppm)): 1.55-1.71 (2H, m), 2.00 (2H, d), 2.21-2.36 (5H, m), 2.40-2.50 (4H, m), 2.50-2.63 (2H, m).

Step 2-4

To a solution of 1.36 g of 4-(2,2-dicyano-5,5,5-trifluoropentyl)cyclohexan-4-one in 15 mL of tetrahydrofuran was added 15 mL of a 0.5 M solution of ethynyl magnesium bromide in tetrahydrofuran at 0° C. under a nitrogen atmosphere, followed by stirring at 0° C. for 5 hours. To the reaction mixture was added 30 mL of a 1 N aqueous hydrochloric acid solution, followed by extraction twice with 30 mL of ethyl acetate. The combined organic layer was washed sequentially with 30 mL of a saturated aqueous sodium hydrogen carbonate solution and 30 mL of a saturated aqueous sodium chloride solution, dried over sodium sulfate, filtered, and then concentrated under reduced pressure. The residue was subjected to silica gel column chromatography to give 0.93 g of 1-(2,2-dicyano-5,5,5-trifluoropentyl)-4-ethynyl-4-hydroxycyclohexane (hereinafter referred to as the present compound (2)) represented by the following formula:

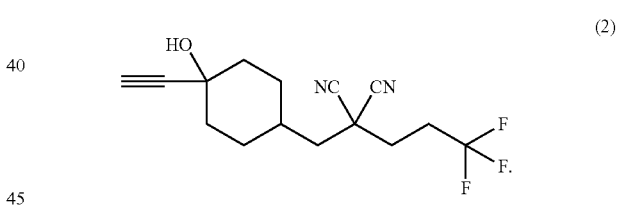

$^1$H-NMR (CDCl$_3$, TMS, δ(ppm)): 1.46-1.56 (2H, m), 1.56-1.67 (2H, m), 1.72-1.84 (2H, m), 2.93 (2H, d), 1.97-2.08 (4H, m), 2.17-2.23 (2H, m), 2.47-2.59 (3H, m).

Production Example 3

A solution of 1.26 g of the present compound (2) in 5 mL of chloroform was cooled to −20° C. under a nitrogen atmosphere. Thereto 0.82 g of diethylaminosulfur trifluoride was added, followed by stirring at room temperature for 5 hours. The reaction mixture was diluted with 20 mL of chloroform. After 20 mL of water was added thereto, an organic layer was separated. An aqueous layer was extracted twice with 20 mL of chloroform. The combined organic layer was washed with 50 mL of a saturated aqueous sodium chloride solution, dried over sodium sulfate, filtered, and then concentrated under reduced pressure. The residue was subjected to silica gel column chromatography to give 0.75 g of 1-(2,2-dicyano-5,5,5-trifluoropentyl)-4-ethynyl-4-fluorocyclohexane (herein after referred to as the present compound (3)) represented by the following formula:

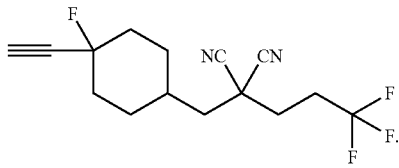

(3)

¹H-NMR (CDCl₃, TMS, δ (ppm)): 1.51-1.57 (2H, m), 1.72-1.93 (7H, m), 2.19-2.30 (4H, m), 2.47-2.59 (3H, m), 2.64 (1H, d).

Production Example 4

Step 4-1

To a solution of 0.60 g of the present compound (3) in 3 mL of tetrahydrofuran was added 3 mL of a 1 M solution of methyl magnesium bromide in tetrahydrofuran at 0° C. under a nitrogen atmosphere, followed by stirring at room temperature for 5 hours. To the reaction mixture was added 30 mL of a 1 N aqueous hydrochloric acid solution, followed by extraction twice with 30 mL of ethyl acetate. The combined organic layer was washed sequentially with 30 mL of a saturated aqueous sodium hydrogen carbonate solution and 30 mL of a saturated aqueous sodium chloride solution, dried over sodium sulfate, filtered, and then concentrated under reduced pressure. The residue was subjected to silica gel column chromatography to give 0.46 g of 4-(2,2-dicyano-5,5,5-trifluoropentyl)-1-ethynylcyclohexene represented by the following formula:

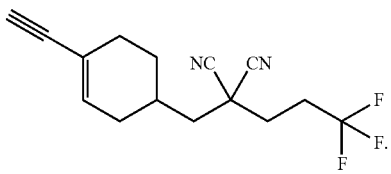 [SMILES: C#CC1=CCC(CC(C#N)(C#N)CCC(F)(F)F)CC1]

¹H-NMR (CDCl₃, TMS, δ (ppm)): 1.46-1.56 (1H, m), 1.78-2.33 (10H, m), 2.44-2.59 (2H, m), 2.85 (1H, s), 6.15 (1H, m).

Step 4-2

To a solution of 0.31 g of 4-(2,2-dicyano-5,5,5-trifluoropentyl)-1-ethynylcyclohexene in 3 mL of chloroform was added 0.23 g of m-chloroperbenzoic acid at 0° C., followed by stirring at room temperature for 5 hours. After the reaction mixture was cooled to 0° C., 5 mL of a 10% aqueous sodium sulfite solution was added thereto, followed by extraction twice with 30 mL of chloroform. The combined organic layer was washed sequentially with 30 mL of a 10% aqueous sodium sulfite solution, 30 mL of a saturated aqueous sodium hydrogen carbonate solution and 30 mL of a saturated aqueous sodium chloride solution, dried over sodium sulfate, filtered, and then concentrated under reduced pressure. The residue was subjected to silica gel column chromatography to give 0.22 g of 4-(2,2-dicyano-5,5,5-trifluoropentyl)-1,2-epoxy-1-ethynylcyclohexane (hereinafter referred to as the present compound (4)) represented by the following formula:

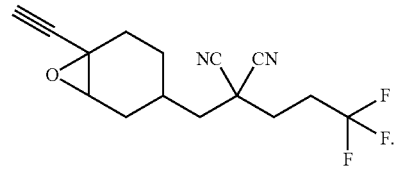 [SMILES: C#CC12CCC(CC(C#N)(C#N)CCC(F)(F)F)CC1O2]

¹H-NMR (CDCl₃, TMS, δ(ppm)): 1.19-1.26 (1H, m), 1.60-2.41 (10H, m), 2.48-2.56 (2H, m), 3.22 (1H, s), 3.45 (1H, m).

Production Example 5

To a solution of 0.12 g of the present compound (1t) in 2 mL of dimethyl sulfoxide were added 0.2 mL of a 40% aqueous dimethylamine solution, 0.2 mL of a 37% aqueous formamide solution and 0.002 g of cuprous iodide, followed by stirring at 70° C. for 8 hours. After the reaction mixture was cooled to room temperature, 10 mL of a saturated aqueous sodium chloride solution was added thereto, followed by extraction three times with 30 mL of ethyl acetate. The combined organic layer was washed twice with 20 mL of a saturated aqueous sodium chloride solution, dried over sodium sulfate, filtered, and then concentrated under reduced pressure. The residue was subjected to silica gel column chromatography to give 0.06 g of the trans-isomer (hereinafter referred to as the present compound (5t)) of 1-(2,2-dicyano-5,5,5-trifluoropentyl)-4-(3-dimethylamino-1-propynyl)cyclohexane (hereinafter referred to as the present compound (5)) represented by the following formula:

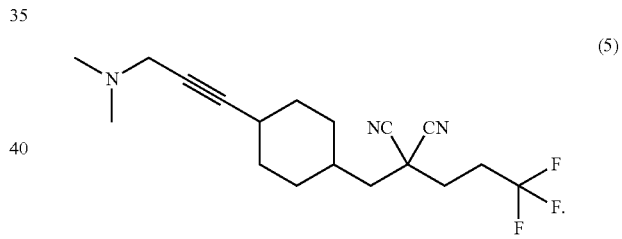

(5)

¹H-NMR (CDCl₃, TMS, δ(ppm)): 1.05-1.20 (2H, m), 1.38-1.56 (2H, m), 1.68-1.84 (1H, m), 1.87 (2H, d), 1.94-2.08 (4H, m), 2.15-2.33 (9H, m), 2.43-2.60 (2H, m), 3.20 (2H, d).

Production Example 6

Step 6-1

A suspension of 0.76 g of lithium aluminum hydride in 10 mL of tetrahydrofuran was cooled to 0° C. under a nitrogen atmosphere. To the suspension was added dropwise a solution of 2.18 g of methyl 1,4-dioxaspiro[4.5]decane-8-acetate in 10 mL of tetrahydrofuran, followed by stirring at room temperature for 3 hours. After the reaction mixture was cooled to 0° C., 1 mL of water was added thereto. The mixture was filtered through celite and then concentrated under reduced pressure. The residue was subjected to silica gel column chromatography to give 1.73 g of 1,4-dioxaspiro[4.5]decane-8-ethanol represented by the following formula:

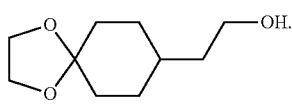

¹H-NMR (CDCl₃, TMS, δ(ppm)): 1.20-1.33 (4H, m), 1.38-1.64 (6H, m), 1.69-1.79 (4H, m), 3.68-3.71 (2H, m), 3.94 (4H, s).

Step 6-2

To a solution of 1.73 g of 1,4-dioxaspiro[4.5]decane-8-ethanol in 10 mL of pyridine was added 1.77 g of p-toluenesulfonyl chloride, followed by stirring at room temperature for 4 hours. To the reaction mixture was added 30 mL of a 1 N aqueous hydrochloric acid solution, followed by extraction twice with 100 mL of ethyl acetate. The combined organic layer was washed sequentially with 30 mL of a 1 N aqueous hydrochloric acid solution, 30 mL of a saturated aqueous sodium hydrogen carbonate solution and 30 mL of a saturated aqueous sodium chloride solution, dried over sodium sulfate, filtered, and then concentrated under reduced pressure. The residue was subjected to silica gel column chromatography to give 2.68 g of 2-(1,4-dioxaspiro[4.5]deca-8-yl)ethyl p-toluenesulfonate represented by the following formula:

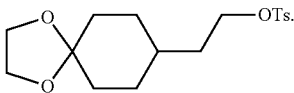

¹H-NMR (CDCl₃, TMS, δ(ppm)): 1.10-1.74 (11H, m), 2.45 (3H, s), 3.87-3.95 (4H, m), 4.03 (2H, dd), 7.34 (2H, d), 7.79 (2H, d).

Step 6-3

To a solution of 2.68 g of 2-(1,4-dioxaspiro[4.5]deca-8-yl) ethyl p-toluenesulfonate in 16 mL of N,N-dimethylformamide were added 1.27 g or 3,3,3-trifluoropropylmalononitrile, 1.31 g of potassium iodide and 1.09 g of potassium carbonate, followed by stirring at 70° C. for 5 hours. After the reaction mixture was cooled to room temperature, 30 mL of a 1 N aqueous hydrochloric acid solution was added thereto, followed by extraction twice with 50 mL of ethyl acetate. The combined organic layer was washed sequentially with 30 mL of a saturated aqueous sodium hydrogen carbonate solution and 30 mL of a saturated aqueous sodium chloride solution, dried over sodium sulfate, filtered, and then concentrated under reduced pressure. The residue was subjected to silica gel column chromatography to give 1.85 g or 8-(3,3-dicyano-6,6,6-trifluorohexyl)-1,4-dioxaspiro[4.5]decane represented by the following formula:

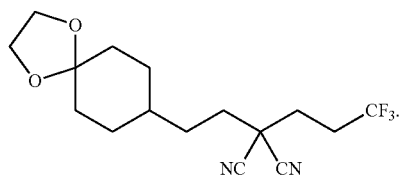 [SMILES: N#CC(C#N)(CCC1CCC2(CC1)OCCO2)CCC(F)(F)F]

¹H-NMR (CDCl₃, TMS, δ(ppm)): 1.23-1.46 (3H, m), 1.46-1.49 (2H, m), 1.58-1.61 (2H, m), 1.70-1.80 (2H, m), 1.97-2.04 (2H, m), 2.17-2.22 (2H, m), 2.45-2.57 (2H, m), 3.92-3.96 (4H, m).

Step 6-4

To 20 mL of a 50% aqueous acetic acid solution, 1.85 g of 8-(3,3-dicyano-6,6,6-trifluorohexyl)-1,4-dioxaspiro[4.5]decane was added, followed by stirring at 50° C. for 8 hours under a nitrogen atmosphere. To the reaction mixture was added 100 mL of water, followed by extraction twice with 100 mL of ethyl acetate. The combined organic layer was washed sequentially with 100 mL of a saturated aqueous sodium hydrogen carbonate solution and 100 mL of a saturated aqueous sodium chloride solution, dried over sodium sulfate, filtered, and then concentrated under reduced pressure. The residue was subjected to silica gel column chromatography to give 1.37 g of 4-(3,3-dicyano-6,6,6-trifluorohexyl)cyclohexanone represented by the following formula:

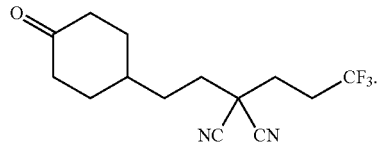 [SMILES: N#CC(C#N)(CCC1CCC(=O)CC1)CCC(F)(F)F]

¹H-NMR (CDCl₃, TMS, δ (ppm)): 1.43-1.55 (2H, m), 1.71-1.79 (2H, m), 1.80-1.92 (1H, m), 2.02-2.14 (4H, m), 2.19-2.27 (2H, m), 2.30-2.60 (6H, m).

Step 6-5

To a solution of 1.14 g of 4-(3,3-dicyano-6,6,6-trifluorohexyl)cyclohexanone in 10 mL of tetrahydrofuran was added 10 mL of a 0.5 M solution of ethynyl magnesium bromide in tetrahydrofuran at 0° C. under a nitrogen atmosphere, followed by stirring at 0° C. for 5 hours. To the reaction mixture was added 30 mL of a 1 N aqueous hydrochloric acid solution, followed by extraction twice with 30 mL of ethyl acetate. The combined organic layer was washed sequentially with 30 mL of a saturated aqueous sodium hydrogen carbonate solution and 30 mL of a saturated aqueous sodium chloride solution, dried over sodium sulfate, filtered, and then concentrated under reduced pressure. The residue was subjected to silica gel column chromatography to give 0.78 g of 1-(3,3-dicyano-6,6,6-trifluorohexyl)-4-ethynyl-4-hydroxycyclohexane (hereinafter referred to as the present compound (6)) represented by the following formula:

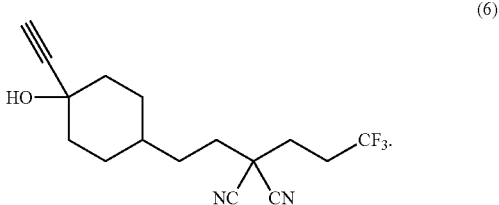 [SMILES: C#CC1(O)CCC(CCC(C#N)(C#N)CCC(F)(F)F)CC1]

(6)

¹H-NMR (CDCl₃, TMS, b (ppm)): 1.30-2.08 (12H, m), 2.19-2.23 (4H, m), 2.45-2.58 (3H, m).

Production Example 7

A solution of 0.78 g of the present compound (6) in 3 mL of chloroform was cooled to −20° C. under a nitrogen atmosphere. Thereto 0.48 g of diethylaminosulfur trifluoride was added, followed by stirring at room temperature for 5 hours. The reaction mixture was diluted with 20 mL of chloroform. After 20 mL of water was added thereto, an organic layer was separated. An aqueous layer was extracted twice with 20 mL of chloroform. The combined organic layer was washed with 50 mL of a saturated aqueous sodium chloride solution, dried over sodium sulfate, filtered, and then concentrated under reduced pressure. The residue was subjected to silica gel column chromatography to give 0.61 g of 1-(3,3-dicyano-6,6,6-trifluorohexyl)-4-ethynyl-4-fluorocyclohexane (hereinafter referred to as the present compound (7)) represented by the following formula:

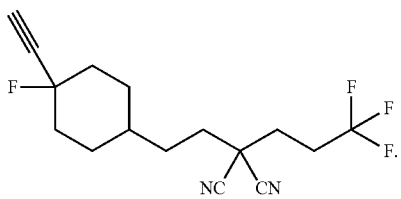

(7)

$^1$H-NMR (CDCl$_3$, TMS, δ (ppm)): 1.30-1.89 (9H, m), 1.97-2.05 (2H, m), 2.14-2.31 (4H, m), 2.45-2.59 (2H, m), 2.63 (1H, d).

Production Example 8

To a solution of 0.82 g of 4-(3,3-dicyano-6,6,6-trifluoropentyl)cyclohexanone in 3 mL of pyridine was added 0.28 g of o-methylhydroxylamine hydrochloride, followed by stirring at room temperature for 4 hours under a nitrogen atmosphere. To the reaction mixture were added 20 mL of ethyl acetate and 20 mL of a 1 N aqueous hydrochloric acid solution, followed by extraction three times with 20 mL of ethyl acetate. The combined organic layer was washed sequentially with 20 mL of a saturated aqueous sodium hydrogen carbonate solution and 20 mL of a saturated aqueous sodium chloride solution, dried over sodium sulfate, filtered, and then concentrated under reduced pressure. The residue was subjected to silica gel column chromatography to give 0.41 g of 4-(2,2-dicyano-5,5,5-trifluoropentyl)-1-(methoxyimino)cyclohexane (hereinafter referred to as the present compound (8)) represented by the following formula:

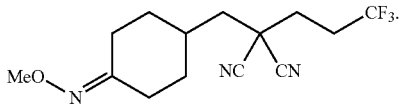

(8)

$^1$H-NMR (CDCl$_3$, TMS, δ (ppm)): 1.24-1.46 (2H, m), 1.77-2.25 (9H, m) 2.41-2.59 (3H, m), 3.21-3.29 (1H, m), 3.83 (3H, s).

Production Example 9

To a solution of 0.27 g of 4-(3,3-dicyano-6,6,6-trifluoropentyl)cyclohexanone in 2 mL of pyridine was added 0.11 g of O-ethylhydroxylamine hydrochloride, followed by stirring at room temperature for 2 hours under a nitrogen atmosphere. To the reaction mixture were added 20 mL of ethyl acetate and 20 mL of a 1 N aqueous hydrochloric acid solution, followed by extraction three times with 20 mL of ethyl acetate. The combined organic layer was washed sequentially with 20 mL of a saturated aqueous sodium hydrogen carbonate solution and 20 mL of a saturated aqueous sodium chloride solution, dried over sodium sulfate, filtered, and then concentrated under reduced pressure. The residue was subjected to silica gel column chromatography to give 0.30 g of 4-(2,2-dicyano-5,5,5-trifluoropentyl)-1-(ethoxyimino)cyclohexane (hereinafter referred to as the present compound (9)) represented by the following formula:

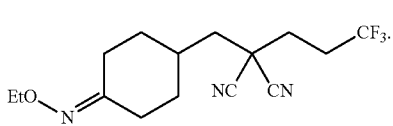

(9)

$^1$H-NMR (CDCl$_3$, TMS, δ (ppm)): 1.25 (3H, t), 1.28-1.44 (2H, m), 1.77-2.26 (9H, m) 2.43-2.60 (3H, m), 3.23-3.33 (1H, m), 4.05 (2H, q).

Production Example 10

To a solution of 0.27 g of 4-(3,3-dicyano-6,6,6-trifluoropentyl)cyclohexanone in 2 mL of pyridine was added 0.16 g of O-t-butylhydroxylamine hydrochloride, followed by stirring at room temperature for 2 hours under a nitrogen atmosphere. To the reaction mixture were added 20 mL of ethyl acetate and 20 mL of a 1 N aqueous hydrochloric acid solution, followed by extraction three times with 20 mL of ethyl acetate. The combined organic layers was washed sequentially with 20 mL of a saturated aqueous sodium hydrogen carbonate solution and 20 mL of a saturated aqueous sodium chloride solution, dried over sodium sulfate, filtered, and then concentrated under reduced pressure. The residue was subjected to silica gel column chromatography to give 0.26 g of 4-(2,2-dicyano-5,5,5-trifluoropentyl)-1-(t-butoxyimino)cyclohexane (hereinafter referred to as the present compound (10)) represented by the following formula:

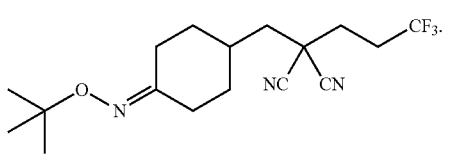

(10)

$^1$H-NMR (CDCl$_3$, TMS, δ (ppm)): 1.25 (9H, s), 1.25-1.37 (2H, m), 1.77-2.24 (9H, m) 2.43-2.57 (3H, m), 3.26-3.33 (1H, m).

Production Example 11

To a solution of 0.27 g of 4-(3,3-dicyano-6,6,6-trifluoropentyl)cyclohexanone in 2 mL of pyridine was added 0.13 g of O-allylhydroxylamine hydrochloride, followed by stirring at room temperature for 2 hours under a nitrogen atmosphere. To the reaction mixture were added 20 mL of ethyl acetate and 20 mL of a 1 N aqueous hydrochloric acid solution, followed by extraction three times with 20 mL of ethyl acetate. The combined organic layer was washed sequentially with 20 mL of a saturated aqueous sodium hydrogen carbonate solution and 20 mL of a saturated aqueous sodium chloride solution, dried over sodium sulfate, filtered, and then concentrated under reduced pressure. The residue was subjected to silica gel column chromatography to give 0.30 g of 4-(2,2-dicyano-5,5,5-trifluoropentyl)-1-(allyloxyimino)cyclohexane (hereinafter referred to as the present compound (11)) represented by the following formula:

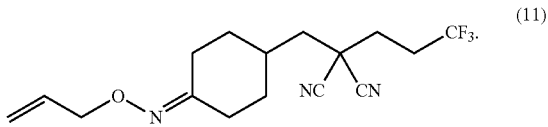 [SMILES: C=CCON=C1CCC(CC(C#N)(C#N)CCC(F)(F)F)CC1]

$^1$H-NMR (CDCl$_3$, TMS, δ (ppm)): 1.23-1.44 (2H, m), 1.74-2.26 (9H, m) 2.43-2.59 (3H, m), 3.27-3.34 (1H, m), 4.51-4.56 (2H, m), 5.16-5.33 (2H, m), 5.92-6.06 (1H, m).

Specific examples of the compound of the present invention are shown below.

A compound represented by the formula (I-a):

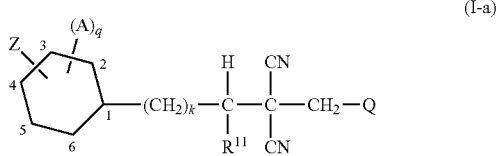

wherein Q, Z, (A)$_q$, R$^{11}$ and k represent any one of combinations shown below. Combinations of Q, Z, (A)$_q$, R$^{11}$ and k for the compound represented by the formula (I-a) are as follows:

[Q, Z, (A)$_q$, R$^{11}$, k]=
[CF$_3$CH$_2$, 4-(HC≡C), -, H, 0],
[CF$_3$CH$_2$, 4-(HC≡CCH$_2$), -, H, 0],
[CF$_3$CH$_2$, 4-(MeC≡C), -, H, 0],
[CF$_3$CH$_2$, 4-(MeOCH$_2$C≡C), -, H, 0],
[CF$_3$CH$_2$, 4-(Me$_2$NCH$_2$C≡C), -, H, 0],
[CF$_3$CH$_2$, 4-(HC≡C), 4-F, H, 0],
[CF$_3$CH$_2$, 4-(HC≡CCH$_2$), 4-F, H, 0],
[CF$_3$CH$_2$, 4-(MeC≡C), 4-F, H, 0],
[CF$_3$CH$_2$, 4-(MeOCH$_2$C≡C), 4-F, H, 0],
[CF$_3$CH$_2$, 4 (Me$_2$NCH$_2$C≡C), 4-F, H, 0],
[CF$_3$CH$_2$, 4-(HC≡C), 4-HO, H, 0],
[CF$_3$CH$_2$, 4-(HC≡CCH$_2$), 4-HO, H, 0],
[CF$_3$CH$_2$, 4-(MeC≡C), 4-HO, H, 0],
[CF$_3$CH$_2$, 4-(MeOCH$_2$C≡C), 4-HO, H, 0],
[CF$_3$CH$_2$, 4-(Me$_2$NCH$_2$C≡C), 4-HO, H, 0],
[CF$_3$CH$_2$, 4-(HC≡C), 3,4-epoxy, H, 0],
[CF$_3$CH$_2$, 4-(HC≡CH$_2$), 3,4-epoxy, H, 0],
[CF$_3$CH$_2$, 4-(MeC≡C), 3,4-epoxy, H, 0],
[CF$_3$CH$_2$, 4-(MeOCH$_2$C≡C), 3,4-epoxy, H, 0],
[CF$_3$CH$_2$, 4-(Me$_2$NCH$_2$C≡C), 3,4-epoxy, H, 0],
[CF$_3$CH$_2$, 4-(HC≡C), -, Me, 0],
[CF$_3$CH$_2$, 4-(HC≡CH$_2$), -, Me, 0],
[CF$_3$CH$_2$, 4-(MeC≡C), -, Me, 0],
[CF$_3$CH$_2$, 4-(MeOCH$_2$C≡C), -, Me, 0],
[CF$_3$CH$_2$, 4-(Me$_2$NCH$_2$C≡C), -, Me, 0],
[CF$_3$CH$_2$, 4-(HC≡C), 4-F, Me, 0],
[CF$_3$CH$_2$, 4-(HC≡CCH$_2$), 4-F, Me, 0],
[CF$_3$CH$_2$, 4-(MeC≡C), 4-F, Me, 0],
[CF$_3$CH$_2$, 4-(MeOCH$_2$C≡C), 4-F, Me, 0],
[CF$_3$CH$_2$, 4-(Me$_2$NCH$_2$C≡C), 4-F, Me, 0],
[CF$_3$CH$_2$, 4-(HC≡C), 4-HO, Me, 0],
[CF$_3$CH$_2$, 4-(HC≡CCH$_2$), 4-HO, Me, 0],
[CF$_3$CH$_2$, (MeC≡C), 4-HO, Me, 0],
[CF$_3$CH$_2$, 4-(MeOCH$_2$C≡C), 4-HO, Me, 0],
[CF$_3$CH$_2$, 4-(Me$_2$NCH$_2$C≡C), 4-HO, Me, 0],
[CF$_3$CH$_2$, 4-(HC-EC), 3,4-epoxy, Me, 0],
[CF$_3$CH$_2$, 4-(HC≡CCH$_2$), 3,4-epoxy, Me, 0],
[CF$_3$CH$_2$, 4-(MeC≡C), 3,4-epoxy, Me, 0],
[CF$_3$CH$_2$, 4-(MeOCH$_2$C≡C), 3,4-epoxy, Me, 0],
[CF$_3$CH$_2$, 4-(Me$_2$NCH$_2$C≡C), 3,4-epoxy, Me, 0],
[CF$_3$CH$_2$, 4-(HC≡C), -, N≡C, 0],
[CF$_3$CH$_2$, 4-(HC≡CCH$_2$), -, N≡C, 0],
[CF$_3$CH$_2$, 4-(MeC≡C), -, N≡C, 0],
[CF$_3$CH$_2$, 4-(MeOCH$_2$C≡C), -, N≡C, 0],
[CF$_3$CH$_2$, 4-(Me$_2$NCH$_2$C≡C), -, N≡C, 0],
[CF$_3$CH$_2$, (HC≡C), 4-F, N≡C, 0],
[CF$_3$CH$_2$, 4-(HC≡CCH$_2$), 4-F, N≡C, 0],
[CF$_3$CH$_2$, (MeC≡C), 4-F, N≡C, 0],
[CF$_3$CH$_2$, 4-(MeOCH$_2$C≡C), 4-F, N≡C, 0],
[CF$_3$CH$_2$, 4-(Me$_2$NCH$_2$C≡C), 4-F, N≡C, 0],
[CF$_3$CH$_2$, (HC-EC), 4-HO, N≡C, 0],
[CF$_3$CH$_2$, 4-(HC≡CCH$_2$), 4-HO, N≡C, 0],
[CF$_3$CH$_2$, (MeC≡C), 4-HO, N≡C, 0],
[CF$_3$CH$_2$, 4-(MeOCH$_2$C≡C), 4-HO, N≡C, 0],
[CF$_3$CH$_2$, 4-(Me$_2$NCH$_2$C≡C), 4-HO, N≡C, 0],
[CF$_3$CH$_2$, 4-(HC≡C), 3,4-epoxy, N≡C, 0],
[CF$_3$CH$_2$, 4-(HC≡CCH$_2$), 3,4-epoxy, N≡C, 0],
[CF$_3$CH$_2$, 4-(MeC≡C), 3,4-epoxy, N≡C, 0],
[CF$_3$CH$_2$, 4-(MeOCH$_2$C≡C), 3,4-epoxy, 0],
[CF$_3$CH$_2$, 4-(Me$_2$NCH$_2$C≡C), 3,4-epoxy, 0],
[CF$_3$CH$_2$, 4-(HC≡C), 3,4-epoxy, N≡C, 0],
[CF$_3$CH$_2$, 4-(HC≡C), -, NH$_2$C(=O), 0],
[CF$_3$CH$_2$, 4-(HC≡CCH$_2$), -, —NH$_2$C(=O), 0],
[CF$_3$CH$_2$, 4-(MeC≡C), -, NH$_2$C(=O), 0],
[CF$_3$CH$_2$, 4-(MeOCH$_2$C≡C), -, NH$_2$C(=O), 0],
[CF$_3$CH$_2$, 4-(Me$_2$NCH$_2$C≡C), -, NH$_2$C(=O), 0],
[CF$_3$CH$_2$, 4-(HC≡C), 4-F, NH$_2$C(=O), 0],
[CF$_3$CH$_2$, 4-(HC≡CH$_2$), 4-F, NH$_2$C(=O), 0],
[CF$_3$CH$_2$, 4-(MeC≡C), 4-F, NH$_2$C(=O), 0],
[CF$_3$CH$_2$, 4-(MeOCH$_2$C≡C), 4-F, NH$_2$C(=O), 0],
[CF$_3$CH$_2$, 4-(Me$_2$NCH$_2$C≡C), 4-F, NH$_2$C(=O), 0],
[CF$_3$CH$_2$, 4-(HC≡C), 4-HO, NH$_2$C(=O), 0],
[CF$_3$CH$_2$, 4-(HC≡CCH$_2$), 4-HO, NH$_2$C(=O), 0],
[CF$_3$CH$_2$, 4-(MeC≡C), 4-HO, NH$_2$C(=O), 0],
[CF$_3$CH$_2$, 4-(MeOCH$_2$C≡C), 4-HO, NH$_2$C(=O), 0],
[CF$_3$CH$_2$, 4-(Me$_2$NCH$_2$C≡C), 4-HO, NH$_2$C(=O), 0],
[CF$_3$CH$_2$, 4-(HC≡C), 3,4-epoxy, NH$_2$C(=O), 0],
[CF$_3$CH$_2$, 4-(HC≡CH$_2$), 3,4-epoxy, NH$_2$C(=O), 0],
[CF$_3$CH$_2$, 4-(MeC≡C), 3,4-epoxy, NH$_2$C(=O), 0],
[CF$_3$CH$_2$, 4-(MeOCH$_2$C≡C), 3,4-epoxy, NH$_2$C(=O)$_r$ 0],
[CF$_3$CH$_2$, 4-(Me$_2$NCH$_2$C≡C), 3,4-epoxy, NH$_2$C(=O), 0],
[CF$_3$CH$_2$, 4-(HC≡C), -, H, 1],
[CF$_3$CH$_2$, 4-(HC≡CCH$_2$), -, H, 1],
[CF$_3$CH$_2$, 4 (MeC≡C), -, H, 1],
[CF$_3$CH$_2$, 4-(MeOCH$_2$C≡C), -, H, 1],
[CF$_3$CH$_2$, 4-(Me$_2$NCH$_2$C≡C), -, H, 1],
[CF$_3$CH$_2$, 4-(HC≡C), 4-F, H, 1],
[CF$_3$CH$_2$, 4-(HC≡CCH$_2$), 4-F, H, 1],
[CF$_3$CH$_2$, 4-(MeC≡C), 4-F, H, 1],
[CF$_3$CH$_2$, 4-(MeOCH$_2$C≡C), 4-F, H, 1],
[CF$_3$CH$_2$, 4-(Me$_2$NCH$_2$C≡C), 4-F, H, 1],
[CF$_3$CH$_2$, 4-(HC≡C), 4-HO, H, 1],
[CF$_3$CH$_2$, 4-(HC≡CH$_2$), 4-HO, H, 1],
[CF$_3$CH$_2$, 4 (MeC≡C), 4-HO, H, 1],
[CF$_3$CH$_2$, 4-(MeOCH$_2$C≡C), 4-HO, H, 1],
[CF$_3$CH$_2$, 4-(Me$_2$NCH$_2$C≡C), 4-HO, H, 1],
[CF$_3$CH$_2$, 4-(HC≡C), 3,4-epoxy, H, 1],
[CF$_3$CH$_2$, 4-(HC≡CCH$_2$), 3,4-epoxy, H, 1],
[CF$_3$CH$_2$, 4-(MeC≡C), 3,4-epoxy, H, 1],
[CF$_3$CH$_2$, 4-(MeOCH$_2$C≡C), 3,4-epoxy, H, 1],
[CF$_3$CH$_2$, 4-(Me$_2$NCH$_2$, 3,4-epoxy, H, 1],

[CF₃CH₂, 4-(HC≡C), 3,4-epoxy, H, 1],
[CF₃, 4-(HC≡C), -, H, 0],
[CF₃, 4-(MeC≡C), -, H, 0],
[CF₃, 4-(Me₂NCH₂C≡C), -, H, 0],
[CF₃, 4-(HC≡C), 4-F, H, 0],
[CF₃, 4-(HC≡C), 4-HO, H, 0],
[CF₃, (HC≡C), 3,4-epoxy, H, 0],
[CF₃CH₂, 3-(HC≡C), -, H, 0],
[CF₃CH₂, (MeC≡C), -, H, 0],
[CF₃CH₂, 3-(Me₂NCH₂C≡C), -, H, 0],
[CF₃CH₂, 3-(HC≡C), 3-F, H, 0],
[CF₃CH₂, (HC≡C), 3-HO, H, 0],
[CF₃CH₂, 3-(HC≡C), 3,4-epoxy, H, 0].

A compound represented by the formula (I-b):

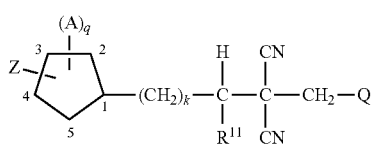

(I-b)

wherein Q, Z, (A)$_q$, R$^{11}$ and k represent any one of combinations shown below. Combinations of Q, Z, (A)$_q$, R$^{11}$ and k for the compound represented by the formula (I-b) are as follows:
[Q, Z, (A)$_q$, R$^{11}$, k]=
[CF₃CH₂, 3-(HC≡C), -, H, 0],
[CF₃CH₂, 3-(HC≡CH₂), -, H, 0],
[CF₃CH₂, 3-(MeC≡C), -, H, 0],
[CF₃CH₂, 3-(MeOCH₂C≡C), -, H, 0],
[CF₃CH₂, 3-(Me₂NCH₂C≡C), -, H, 0],
[CF₃CH₂, 3-(HC≡C), 3-F, H, 0],
[CF₃CH₂, 3-(HC≡CCH₂), 3-F, H, 0],
[CF₃CH₂, 3-(MeC≡C), 3-F, H, 0],
[CF₃CH₂, 3-(MeOCH₂C≡C), 3-F, H, 0],
[CF₃CH₂, 3-(Me₂NCH₂C≡C), 3-F, H, 0],
[CF₃CH₂, 3-(HC≡C), 3-HO, H, 0],
[CF₃CH₂, 3-(HC≡CCH₂), 3-HO, H, 0],
[CF₃CH₂, 3-(MeC≡C), 3-HO, H, 0],
[CF₃CH₂, 3-(MeOCH₂C≡C), 3-HO, H, 0],
[CF₃CH₂, 3-(Me₂NCH₂C≡C), 3-HO, H, 0],
[CF₃CH₂, 3-(HC≡C), 3,4-epoxy, H, 0],
[CF₃CH₂, 3-(HC≡CCH₂), 3,4-epoxy, H, 0],
[CF₃CH₂, 3-(MeC≡C), 3,4-epoxy, H, 0],
[CF₃CH₂, 3-(MeOCH₂C≡C), 3,4-epoxy, H, 0],
[CF₃CH₂, 3-(Me₂NCH₂C≡C), 3,4-epoxy, H, 0],
[CF₃CH₂, 3-(HC≡C), -, Me, 0],
[CF₃CH₂, 3-(HC≡CCH₂), -, Me, 0],
[CF₃CH₂, 3-(MeC≡C), -, Me, 0],
[CF₃CH₂, 3-(MeOCH₂C≡C), -, Me, 0],
[CF₃CH₂, 3-(Me₂NCH₂C≡C), -, Me, 0],
[CF₃CH₂, 3-(HC≡C), 3-F, Me, 0],
[CF₃CH₂, 3-(HC≡CCH₂), 3-F, Me, 0],
[CF₃CH₂, 3-(MeC≡C), 3-F, Me, 0],
[CF₃CH₂, 3-(MeOCH₂C≡C), 3-F, Me, 0],
[CF₃CH₂, 3-(Me₂NCH₂C≡C), 3-F, Me, 0],
[CF₃CH₂, 3-(HC≡C), 3-HO, Me, 0],
[CF₃CH₂, 3-(HC≡CCH₂), 3-HO, Me, 0],
[CF₃CH₂, 3-(MeC≡C), 3-HO, Me, 0],
[CF₃CH₂, 3-(MeOCH₂C≡C), 3-HO, Me, 0],
[CF₃CH₂, 3-(Me₂NCH₂C≡C), 3-HO, Me, 0],
[CF₃CH₂, 3-(HC≡C), 3,4-epoxy, Me, 0],
[CF₃CH₂, 3-(HC≡CCH₂), 3,4-epoxy, Me, 0],
[CF₃CH₂, 3-(MeC≡C), 3,4-epoxy, Me, 0],
[CF₃CH₂, 3-(MeOCH₂C≡C), 3,4-epoxy, Me, 0],
[CF₃CH₂, 3-(Me₂NCH₂C≡C), 3,4-epoxy, Me, 0],
[CF₃CH₂, 3-(HC≡C), -, N≡C, 0],
[CF₃CH₂, 3-(HC≡CCH₂), -, N≡C, 0],
[CF₃CH₂, 3-(MeC≡C), -, N≡C, 0],
[CF₃CH₂, 3-(MeOCH₂C≡C), -, N≡C, 0],
[CF₃CH₂, 3-(Me₂NCH₂C≡C), -, N≡C, 0],
[CF₃CH₂, 3-(HC≡C), 3-F, N≡C, 0],
[CF₃CH₂, 3-(HC≡CCH₂), 3-F, N≡C, 0],
[CF₃CH₂, 3-(MeC≡C), 3-F, N≡C, 0],
[CF₃CH₂, 3-(MeOCH₂C≡C), 3-F, N≡C, 0],
[CF₃CH₂, 3-(Me₂NCH₂C≡C), 3-F, N≡C, 0],
[CF₃CH₂, 3-(HC≡C), 3-HO, N≡C, 0],
[CF₃CH₂, 3-(HC≡CCH₂), 3-HO, N≡C, 0],
[CF₃CH₂, 3-(MeC≡C), 3-HO, N≡C, 0],
[CF₃CH₂, 3-(MeOCH₂C≡C), 3-HO, N≡C, 0],
[CF₃CH₂, 3-(Me₂NCH₂C≡C), 3-HO, N≡C, 0],
[CF₃CH₂, 3-(HC≡C), 3,4-epoxy, N≡C, 0],
[CF₃CH₂, 3-(HC≡CCH₂), 3,4-epoxy, N≡C, 0],
[CF₃CH₂, 3-(MeC≡C), 3,4-epoxy, N≡C, 0],
[CF₃CH₂, 3-(MeOCH₂C≡C), 3,4-epoxy, N≡C, 0],
[CF₃CH₂, 3-(Me₂NCH₂C≡C), 3,4-epoxy, 0],
[CF₃CH₂, 3-(HC≡C), 3,4-epoxy, N≡C, 0],
[CF₃CH₂, 3-(HC≡C), -, NH₂C(=O), 0],
[CF₃CH₂, 3-(HC≡CCH₂), -, NH₂C(=O), 0],
[CF₃CH₂, 3-(MeC≡C), -, NH₂C(=O), 0],
[CF₃CH₂, 3-(MeOCH₂C≡C), -, NH₂C(=O), 0],
[CF₃CH₂, 3-(Me₂NCH₂C≡C), -, NH₂C(=O), 0],
[CF₃CH₂, 3-(HC≡C), 3-F, NH₂C(=O), 0],
[CF₃CH₂, 3-(HC≡CCH₂), 3-F, NH₂C(=O), 0],
[CF₃CH₂, 3-(MeC≡C), 3-F, NH₂C(=O), 0],
[CF₃CH₂, 3-(MeOCH₂C≡C), 3-F, NH₂C(=O), 0],
[CF₃CH₂, 3-(Me₂NCH₂C≡C), 3-F, NH₂C(=O), 0],
[CF₃CH₂, 3-(HC≡C), 3-HO, NH₂C(=O), 0],
[CF₃CH₂, 3-(HC≡CCH₂), 3-HO, NH₂C(=O), 0],
[CF₃CH₂, 3-(MeC≡C), 3-HO, NH₂C(=O), 0],
[CF₃CH₂, 3-(MeOCH₂C≡C), 3-HO, NH₂C(=O), 0],
[CF₃CH₂, 3-(Me₂NCH₂C≡C), 3-HO, NH₂C(=O), 0],
[CF₃CH₂, 3-(HC≡C), 3,4-epoxy, NH₂C(=O), 0],
[CF₃CH₂, 3-(HC≡CCH₂), 3,4-epoxy, NH₂C(=O), 0],
[CF₃CH₂, 3-(MeC≡C), 3,4-epoxy, NH₂C(=O), 0],
[CF₃CH₂, 3-(MeOCH₂C≡C), 3,4-epoxy, NH₂C(=O), 0],
[CF₃CH₂, 3-(Me₂NCH₂C≡C), 3,4-epoxy, NH₂C(=O), 0],
[CF₃CH₂, 3-(HC≡C), -, H, 1],
[CF₃CH₂, 3-(HC≡CCH₂), -, H, 1],
[CF₃CH₂, 3-(MeC≡C), -, H, 1],
[CF₃CH₂, 3-(MeOCH₂C≡C), -, H, 1],
[CF₃CH₂, 3-(Me₂NCH₂C≡C), -, H, 1],
[CF₃CH₂, 3-(HC≡C), 3-F, H, 1],
[CF₃CH₂, 3-(HC≡CCH₂), 3-F, H, 1],
[CF₃CH₂, 3-(MeC≡C), 3-F, H, 1],
[CF₃CH₂, 3-(MeOCH₂C≡C), 3-F, H, 1],
[CF₃CH₂, 3-(Me₂NCH₂C≡C), 3-F, H, 1],
[CF₃CH₂, 3-(HC≡C), 3-HO, H, 1],
[CF₃CH₂, 3-(HC≡CCH₂), 3-HO, H, 1],
[CF₃CH₂, 3-(MeC≡C), 3-HO, H, 1],
[CF₃CH₂, 3-(MeOCH₂C≡C), 3-HO, H, 1],
[CF₃CH₂, 3-(Me₂NCH₂C≡C), 3-HO, H, 1],
[CF₃CH₂, 3-(HC-EC), 3,4-epoxy, H, 1],
[CF₃CH₂, 3-(HC≡CCH₂), 3,4-epoxy, H, 1],
[CF₃CH₂, 3-(MeC≡C), 3,4-epoxy, H, 1],
[CF₃CH₂, 3-(MeOCH₂C≡C), 3,4-epoxy, H, 1],
[CF₃CH₂, 3-(Me₂NCH₂C≡C), 3,4-epoxy, H, 1],
[CF₃CH₂, 3-(HC≡C), 3,4-epoxy, H, 1],
[CF₃, 3-(HC≡C), -, H, 0],
[CF₃, 3-(MeC≡C), -, H, 0],
[CF₃, 3-(Me₂NCH₂C≡C), -, H, 0],
[CF₃, 3-(HC≡C), 3-F, H, 0],

[CF$_3$, 3-(HC≡C), 3-HO, H, 0],
[CF$_3$, 3-(HC≡C), 3,4-epoxy, H, 0].

A compound represented by the formula (I-c):

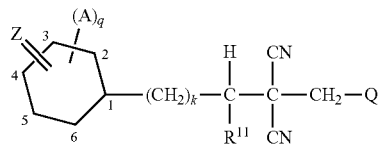

wherein Q, Z, (A)$_q$, R$^{11}$ and k represent any one of combinations shown below. Combinations of Q, Z, (A)$_q$, R$^{11}$ and k for the compound represented by the formula (I-c) are as follows:

[Q, Z, (A)$_q$, R$^{11}$, k]=
[CF$_3$CH$_2$, 4-(MeO—N), -, H, 0],
[CF$_3$CH$_2$, 4-(EtO—N), -, H, 0],
[CF$_3$CH$_2$, 4-(tBuO—N), -, H, 0],
[CF$_3$CH$_2$, 4-(CH$_2$=CHCH$_2$O—N), -, H, 0],
[CF$_3$CH$_2$, 4-(MeO—N), -, Me, 0],
[CF$_3$CH$_2$, 4-(EtO—N), -, Me, 0],
[CF$_3$CH$_2$, 4-(tBuO—N), -, Me, 0],
[CF$_3$CH$_2$, 4-(CH$_2$=CHCH$_2$O—N), -, Me, 0].

As used herein, abbreviations have the following meanings.

Me: methyl group, Et: ethyl group, Pr: propyl group, tBu: butyl group, -: no substituent (q=0 in this case)

Next, Formulation Examples are shown. The term "part(s)" means part(s) by weight. The compounds of the present invention are represented by the compound numbers as described above.

Formulation Example 1

Nine parts of any one of the present compounds (1t), (1c) and (2) to (11) is dissolved in 37.5 parts of xylene and 37.5 parts of dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 2

Five parts of the present compound (1t) or the present compound (1c) and 4 parts of a compound selected from the following group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

The group [A]: aluminium phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, acrinathrin, allethrin, beta-cyfluthrin, bifenthrin, cycloprothrin, cyfluthrin, cyhalothrin, empenthrin, deltamethrin, esfenvalerate, ethofenprox, fenvalerate, flucythrinate, flufenoprox, flumethrin, fluvalinate, halfenprox, imiprothrin, prallethrin, pyrethrins, resmethrin, sigma-cypermethrin, silafluofen, tefluthrin, tralomethrin, transfluthrin, tetramethrin, lambda-cyhalothrin, gamma-cyhalothrin, furamethrin, tau-fluvalinate, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, cartap, bensultap, thiocyclam, monosultap, bisultap, imidacloprid, nitenpyram, acetamiprid, thiamethoxam, thiacloprid, chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron, acetoprole, fipronil, vaniliprole, pyriprole, pyrafluprole, chromafenozide, halofenozide, methoxyfenozide, tebufenozide, aldrin, dieldrin, dienochlor, endosulfan, methoxychlor, nicotine-sulfate, avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, chlorantraniliprole, tralopyril, a compound represented by the following formula (A):

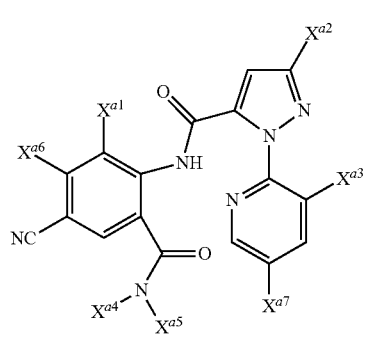

wherein X$^{a1}$ represents a methyl group, a chlorine atom, a bromine atom or a fluorine atom, X$^{a2}$ represents a fluorine atom, a chlorine atom, a bromine atom, a C1-C4 haloalkyl group or a C1-C4 haloalkoxy group, X$^{a3}$ represents a fluorine atom, a chlorine atom or a bromine atom, X$^{a4}$ represents an optionally substituted C1-C4 alkyl, an optionally substituted C3-C4 alkenyl, an optionally substituted C3-C4 alkynyl, an optionally substituted C3-C5 cycloalkylalkyl or a hydrogen atom, X$^{a5}$ represents a hydrogen atom or a methyl group, X$^{a6}$ represents a hydrogen atom, a fluorine atom or a chlorine atom, and $X^{a7}$ represents a hydrogen atom, a fluorine atom or a chlorine atom; a compound represented by the following formula (B):

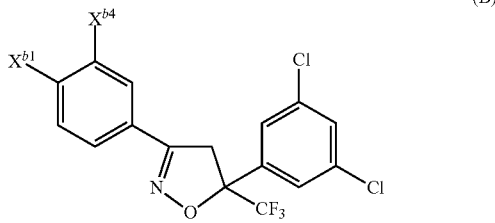

(B)

wherein $X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group or an optionally substituted 1,2,4-triazol-1-yl group, $X^{b2}$ represents an optionally substituted C1-C4 haloalkyl group such as a 2,2,2-trifluoroethyl group or an optionally substituted C3-C6 cycloalkyl group such as a cyclopropyl group, $X^{b3}$ represents an optionally substituted C1-C4 alkyl group such as methyl, and $X^{b4}$ represents a hydrogen atom, a chloro atom, a cyano group or a methyl group; and a compound represented by the following formula (C):

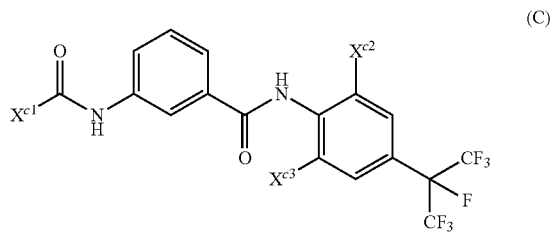

(C)

wherein $X^{c1}$ represents an optionally substituted C1-C4 alkyl group such as a 3,3,3-trifluoropropyl group, an optionally substituted C1-C4 alkoxy group such as a 2,2,2-trichloroethoxy group, an optionally substituted phenyl group such as a 4-cyanophenyl group, or an optionally substituted pyridyl group such as a 2-chloro-3-pyridyl group, $X^{c2}$ represents a methyl group or a trifluoromethyl group, and $X^{c3}$ represents a methyl group or a halogen atom; acequinocyl, amitraz, benzoximate, bifenaate, bromopropylate, chinomethionat, chlorobenzilate, CPCBS (chlorfenson), clofentezine, cyflumetofen, kelthane (dicofol), fenbutatin oxide, fenothiocarb, fenpyroximate, fluacrypyrim, fluproxyfen, hexythiazox, propargite (BPPS), pyridaben, pyrimidifen, tebufenpyrad, tetradifon, spirodiclofen, spiromesifen, spirotetramat, amidoflumet, cyenopyrafen.

Formulation Example 3

Five parts of the present compound (2) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 4

Five parts of the present compound (3) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 5

Five parts of the present compound (4) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 6

Five parts of the present compound (5) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 7

Five parts of the present compound (6) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 8

Five parts of the present compound (7) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 9

Five parts of the present compound (8) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 10

Five parts of the present compound (9) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 11

Five parts of the present compound (10) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 12

Five parts of the present compound (11) and 4 parts of a compound selected from the group [A] are dissolved in 37.5 parts of xylene and 37.5 parts of N,N-dimethylformamide. Thereto. 10 parts of polyoxyethylene styryl phenyl ether and 6 parts of calcium dodecylbenzenesulfonate are added and mixed by stirring thoroughly to obtain an emulsifiable concentrate.

Formulation Example 13

Five parts of SORPOL 5060 (registered trade name for TOHO Chemical Industry Co., LTD.) is added to 40 parts of any one of the present compounds (1t), (1c) and (2) to (11) and mixed thoroughly. The mixture is mixed with 32 parts of CARPLEX #80 (registered trade name for Shionogi & Co., Ltd., synthetic hydrous silicon oxide fine powder) and 23 parts of 300 mesh diatomaceous earth by using a juice mixer to obtain a wettable powder.

Formulation Example 14

Three parts of any one of the present compounds (1t), (1c) and (2) to (11), 5 parts of synthetic hydrous silicon oxide fine powder, 5 parts of sodium dodecylbenzenesulfonate, 30 parts of bentonite and 57 parts of clay are mixed by stirring thoroughly. To this mixture an appropriate amount of water is added. The mixture is further stirred, granulated with a granulator, and then air-dried to obtain a granule.

Formulation Example 15

Four point five parts of any one of the present compounds (1t), (1c) and (2) to (11), 1 part of synthetic hydrous silicon oxide fine powder, 1 part of Dorires B (manufactured by Sankyo) as a flocculant, and 7 parts of clay are mixed thoroughly in a mortar, and then mixed by stirring by using a juice mixer. To the resultant mixture 86.5 parts of cut clay is added and mixed by stirring thoroughly to obtain a dust.

Formulation Example 16

Ten parts of any one of the present compounds (1t), (1c) and (2) to (11), 35 parts of white carbon containing 50% by weight of polyoxyethylene alkylether sulfate ammonium salt, and 55 parts of water are mixed and then finely-divided by a wet grinding method to obtain a formulation.

Formulation Example 17

Zero point five part of any one of the present compounds (1t), (1c) and (2) to (11) is dissolved in 10 parts of dichloromethane. This solution is mixed with 89.5 parts of Isopar M (isoparaffin: registered trade name for Exxon Chemical) to obtain an oil solution.

Formulation Example 18

Zero point one part of any one of the present compounds (1t), (1c) and (2) to (11) and 49.9 parts of NEO-THIOZOL (Chuo Kasei Co., Ltd.) are placed in an aerosol can. An aerosol valve is fitted to the can. The can is charged with 25 parts of dimethyl ether and 25 parts of LPG, and then shaken. An actuator is fitted to the can to obtain an oily aerosol.

Formulation Example 19

Zero point six parts of any one of the present compounds (1t), (1c) and (2) to (11), 0.01 part of BHT, 5 parts of xylene, 3.39 parts of a deodorized kerosine and 1 part of an emulsifying agent [Atmos 300 (registered trade name for Atmos Chemical Ltd.)] are mixed to obtain a solution. An aerosol container is charged with the obtained solution and 50 parts of distilled water. A valve part is attached to the container and the container is then charged with 40 parts of a propellant (LPG) through the valve under increased pressure to obtain an aqueous aerosol.

Formulation Example 20

Five parts of any one of the present compounds (1t), (1c) and (2) to (11) are dissolved in 80 parts of diethylene glycol monoethyl ether. Thereto 15 parts of propylene carbonate is mixed to obtain a spot-on liquid formulation.

Formulation Example 21

Ten parts of any one of the present compounds (1t), (1c) and (2) to (11) are dissolved in 70 parts of diethylene glycol monoethyl ether. Thereto 20 parts of 2-octyldodecanol is mixed to obtain a pour-on liquid formulation.

Formulation Example 22

To 0.5 parts of any one of the present compounds (1t), (1c) and (2) to (11) are added 60 parts of NIKKOL TEALS-42 (a 42% aqueous solution of triethanolamine lauryl sulfate, Nikko Chemicals) and 20 parts of propylene glycol. The mixture is stirred well to obtain a homogeneous solution. Thereto 19.5 parts of water is added and mixed by stirring thoroughly to obtain a homogeneous shampoo formulation.

Formulation Example 23

A porous ceramic plate with a length of 4.0 cm, a width of 0.4 cm and a thickness of 1.2 cm is impregnated with a solution of 0.1 g of any one of the present compounds (1t), (1c) and (2) to (11) in 2 ml of propylene glycol to obtain a heating-type smoking agent.

Formulation Example 24

Five parts of any one of the present compounds (1t), (1c) and (2) to (11) and 95 parts of an ethylene-methyl methacrylate copolymer (the proportion of methyl methacrylate in the copolymer: 10% by weight, ACRYFT WD301, Sumitomo Chemical) are melted and kneaded in a sealed pressure kneader (Moriyama Manufacturing Co., Ltd.). The obtained kneaded product is extruded through a molding die of an extruder to obtain a molded bar with a length of 15 cm and a diameter of 3 mm.

Formulation Example 25

Five parts of any one of the present compounds (1t), (1c) and (2) to (11) and 95 parts of a flexible polyvinyl chloride resin are melted and kneaded in a sealed pressure kneader (Moriyama Manufacturing Co., Ltd.). The obtained kneaded product is extruded through a molding die of an extruder to obtain a molded bar with a length of 15 cm and a diameter of 3 mm.

Test Example 1

A formulation of any one of the present compounds (1t), (1c), (3), (4), (7), (8), (9), (10) and (11) obtained according to Formulation Example 16 was diluted with water to prepare a test solution having 500 ppm of the active ingredient.

Separately, 50 g of culture soil, Bonsol No. 2 (manufactured by Sumitomo Chemical Co., Ltd.) was put into a polyethylene cup, and 10 to 15 seeds of rice were planted therein. The rice plants were grown until the second foliage leaf was developed, and then cut into 5 cm height. The test solution was sprayed on the rice paints in the amount of 20 ml/cup.

After the test solution sprayed on the rice plants was dried, the rice plants were placed in a plastic cup for the purpose of preventing test worms from escaping. Thirty (30) first-instar larvae of *Nilaparvata lugens* were released into the cup, and the cup was sealed with a lid. Then the cup was placed in a greenhouse at 25° C. for 6 days. Then, the number of *Nilaparvata lugens* parasitic on the rice plants was counted.

As a result, on the plants treated with any one of the present compounds (1t), (1c), (3), (4), (7), (8), (9), (10) and (11), the number of the parasitic pests was 3 or smaller.

Test Example 2

A formulation of any one of the present compounds (1t), (1c), (2), (3), (4), (8), (9) and (11) obtained according to Formulation Example 16 was diluted with water to prepare a test solution having 55.6 ppm of the active ingredient.

Separately, 50 g of culture soil, Bonsol No. 2 (manufactured by Sumitomo Chemical Co., Ltd.) was put into a polyethylene cup with five holes 5 mm in diameter at the bottom, and 10 to 15 seeds of rice were planted therein. The rice plants were grown until the second foliage leaf was developed, and then treated with 45 ml of the test solution by allowing the plants to absorb the test solution from the bottom of the cup. The rice plants were placed in a greenhouse at 25° C. for 6 days and then cut into the same height of 5 cm. Thirty (30) first-instar larvae of *Nilaparvata lugens* were released into the cup, and the cup was sealed with a lid. Then the cup was left at 25° C. for 6 days. Then, the number of *Nilaparvata lugens* parasitic on the rice plants was counted.

As a result, on the plants treated with any one of the present compounds (1t), (1c), (2), (3), (4), (8), (9) and (11), the number of the parasitic pests was 3 or smaller.

Test Example 3

A formulation of any one of the present compounds (1t), (1c), (3), (4), (8) and (9) obtained according to Formulation Example 16 was diluted with water to prepare a test solution having 500 ppm of the active ingredient.

Separately, cucumber was planted in a polyethylene cup and was grown until the first foliage leaf was developed, on which about 20 individuals of *Aphis gossypii* were placed. After 1 day, the test solution was sprayed on the cucumber in the amount of 20 ml/cup. After 6 days, the number of *Aphis gossypii* was counted.

As a result, on the cucumber treated with any one of the present compounds (1t), (1c), (3), (4), (8) and (9), the number of the parasitic pests was 3 or smaller.

Test Example 4

A formulation of any one of the present compounds (1t), (1c), (2), (3), (4), (7), (8), (9) and (10) obtained according to Formulation Example 16 was diluted with water to prepare a test solution having 500 ppm of the active ingredient.

A filter paper having a diameter of 5.5 cm was spread on the bottom of a polyethylene cup having a diameter of 5.5 cm and 0.7 ml of the test solution was added dropwise onto the filter paper. As a bait, 30 mg of sucrose was uniformly placed on the filter paper. Into the polyethylene cup, 10 female imagoes of *Musca domestica* were released and the cup was sealed with a lid. After 24 hours, the number of surviving or dead *Musca domestica* was counted and the death rate of the pest was calculated.

As a result, the treatment with any one of the present compounds (1t), (1c), (2), (3), (4), (7), (8), (9) and (10) showed a pest death rate of 90% or more.

Test Example 5

A formulation of any one of the present compounds (1t), (1c), (3), (4), (7) and (8) obtained according to Formulation Example 16 was diluted with water to prepare a test solution having 500 ppm of the active ingredient.

A filter paper having a diameter of 5.5 cm was spread on the bottom of a polyethylene cup having a diameter of 5.5 cm and 0.7 ml of the test solution was added dropwise onto the filter paper. As a bait, 30 mg of sucrose was uniformly placed on the filter paper. Into the polyethylene cup, 2 male imagoes of *Blattalla germanica* were released and the cup was sealed with a lid. After 6 days, the number of surviving or dead *Blattalla germanica* was counted and the death rate of the pest was calculated.

As a result, the treatment with any one of the present compounds (1t), (1c), (3), (4), (7) and (8) showed a pest death rate of 100%.

Test Example 6

A formulation of any one of the present compounds (1t), (1c), (3), (4), (8), (9) and (11) obtained according to Formulation Example 16 was diluted with water to prepare a test solution having 500 ppm of the active ingredient.

To 100 mL of ion-exchanged water, 0.7 ml of the test solution was added (active ingredient concentration: 3.5 ppm). Into the solution, 20 last-instar larvae of *Culex pipiens pallens* were released. After 1 day, the number of surviving or dead *Culex pipiens pallens* was counted and the death rate of the pest was calculated.

As a result, the treatment with any one of the present compounds (1t), (1c), (3), (4), (8), (9) and (11) showed a pest death rate of 95% or more.

Test Example 7

In 10 mL of acetone was dissolved 25 mg of a formulation of any one of the present compounds (1t), (1c), (3) and (4) obtained according to Formulation Example 16 to obtain an acetone solution. To one surface of a filter paper (TOYO No. 2; 5×10 cm), 1 mL of the acetone solution was applied uniformly (i.e., the filter paper had a surface area of 50 cm², and therefore, the application amount of the compound of the present invention was 500 mg/m$^2$). After drying, the filter paper was folded into two and the two sides were clipped to make a pouch. Into the pouch, test mites (*Haemaphysalis longicornis*, non-blood sucking young mites, 10 mites per group) were released. The open part of the pouch was closed tightly with clips, and after 2 days, death of mites was examined.

As a result, the treatment with any one of the present compounds (1t), (1c), (3) and (4) showed a pest death rate of 90% or more.

INDUSTRIAL APPLICABILITY

The compound of the present invention has an excellent control effect on arthropod pests, and is therefore useful as an active ingredient of a pesticidal composition.

The invention claimed is:
1. A nitrile compound represented by the formula (I):

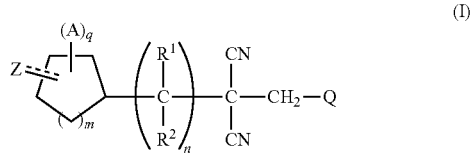

wherein m represents an integer of 2; n represents an integer of 1 to 4; q represents an integer of 0 to 4;
Q represents a C1-C4 fluoroalkyl group;
Z represents a =N—OR$^3$ group, or a C2-C6 alkynyl group optionally substituted with a group selected from the group L;
R$^1$ and R$^2$ independently represent —C(=G)R$^5$, a cyano group, a halogen atom, a hydrogen atom, or a monovalent C1-C4 chain hydrocarbon group optionally substituted with a halogen atom;
A represents —OR$^6$, —SR$^6$, —S(=O)R$^6$, —S(=O)$_2$R$^6$, —C(=O)R$^7$, —OC(=O)R$^8$, a halogen atom, a cyano group, a hydroxyl group, a monovalent C1-C6 chain hydrocarbon group optionally substituted with a group selected from the group L, or a C3-C6 cycloalkyl group optionally substituted with a halogen atom, and when q is 2 or more, two A's optionally form together a C2-C6 alkanediyl group, a C4-C6 alkenediyl group, -G-, -G-T$^1$-G-, or -G-T$^1$-G-T$^2$-;
said C2-C6 alkanediyl group or said C4-C6 alkenediyl group is optionally substituted with a group selected from the group L;
G represents an oxygen atom or a sulfur atom;
T$^1$ and T$^2$ independently represent a methylene group or a C2-C6 alkanediyl group;
R$^3$ represents a hydrogen atom, or a C1-C6 chain hydrocarbon group optionally substituted with a halogen atom;
R$^5$ represents a hydroxyl group, an amino group, a C2-C5 cyclic amino group, a hydrogen atom, a C1-C4 alkyl group optionally substituted with a halogen atom, a C1-C4 alkoxy group optionally substituted with a halogen atom, a C3-C6 alkenyloxy group optionally substituted with a halogen atom, a C3-C6 alkynyloxy group optionally substituted with a halogen atom, a C1-C4 alkylamino group optionally substituted with a halogen atom, or a di(C1-C4 alkyl)amino group optionally substituted with a halogen atom;

R$^6$ represents a C1-C4 alkyl group optionally substituted with a halogen atom, or a C3-C6 cycloalkyl group optionally substituted with a halogen atom;
the group L consists of a hydroxyl group, —N(R$^9$)R$^{10}$, a C2-C5 cyclic amino group, —C(=O)R$^7$, —OC(=O)R$^8$, a halogen atom, a C1-C4 alkoxy group optionally substituted with a halogen atom, a C3-C6 alkenyloxy group optionally substituted with a halogen atom, and a C3-C6 alkynyloxy group optionally substituted with a halogen atom;
R$^7$ represents a hydroxyl group, a C2-C5 cyclic amino group, an amino group, a hydrogen atom, a C1-C4 alkoxy group optionally substituted with a halogen atom, a C3-C6 alkenyloxy group optionally substituted with a halogen atom, a C3-C6 alkynyloxy group optionally substituted with a halogen atom, a C1-C4 alkylamino group optionally substituted with a halogen atom, a di(C1-C4 alkyl)amino group optionally substituted with a halogen atom, or a C1-C4 alkyl group optionally substituted with a halogen atom;
R$^8$ represents a C2-C5 cyclic amino group, an amino group, a hydrogen atom, a C1-C4 alkoxy group optionally substituted with a halogen atom, a C3-C6 alkenyloxy group optionally substituted with a halogen atom, a C3-C6 alkynyloxy group optionally substituted with a halogen atom, a C1-C4 alkylamino group optionally substituted with a halogen atom, a di(C1-C4 alkyl)amino group optionally substituted with a halogen atom, or a C1-C4 alkyl group optionally substituted with a halogen atom; and
R$^9$ and R$^{10}$ independently represent a hydrogen atom, a C1-C4 alkyl group optionally substituted with a halogen atom, a C3-C6 alkenyl group optionally substituted with a halogen atom, a C3-C6 alkynyl group optionally substituted with a halogen atom, a C3-C6 cycloalkyl group optionally substituted with a halogen atom, or a phenyl group optionally substituted with a halogen atom.

2. The nitrile compound according to claim 1, wherein Z is the C2-C5 alkynyl group optionally substituted with a group selected from the group L.

3. The nitrile compound according to claim 1, wherein Z is a —C≡C—R$^4$ group and R$^4$ is a C1-C4 alkyl group or a hydrogen atom.

4. The nitrile compound according to claim 1, wherein Z is an ethynyl group.

5. The nitrile compound according to claim 1, wherein Z is the =N—OR$^3$ group and R$^3$ is the C1-C6 chain hydrocarbon group.

6. The nitrile compound according to claim 1, wherein Q is a 2,2,2-trifluoroethyl group.

7. The nitrile compound according to claim 1, wherein n is 1.

8. The nitrile compound according to claim 1, wherein n is 1 and R$^1$ and R$^2$ are hydrogen atoms.

9. A pesticidal composition comprising the nitrile compound according to claim 1 as an active ingredient.

10. A method for controlling an arthropod pest which comprises applying an effective amount of the nitrile compound according to claim 1 to the arthropod pest or a habitat of the arthropod pest.

* * * * *